(12) United States Patent
Zheng et al.

(10) Patent No.: US 11,172,673 B2
(45) Date of Patent: *Nov. 16, 2021

(54) PLATELET STORAGE METHODS AND COMPOSITIONS FOR SAME

(71) Applicants: Children's Hospital Medical Center, Cincinnati, OH (US); University of Cincinnati, Cincinnati, OH (US)

(72) Inventors: Yi Zheng, Cincinnati, OH (US); Jose Cancelas, Cincinnati, OH (US)

(73) Assignees: CHILDREN'S HOSPITAL MEDICAL CENTER, Cincinnati, OH (US); UNIVERSITY OF CINCINNATI, Cincinnati, OH (US)

(*) Notice: Subject to any disclaimer, the term of this patent is extended or adjusted under 35 U.S.C. 154(b) by 415 days.

This patent is subject to a terminal disclaimer.

(21) Appl. No.: 16/041,026

(22) Filed: Jul. 20, 2018

(65) Prior Publication Data

US 2019/0021307 A1 Jan. 24, 2019

Related U.S. Application Data

(63) Continuation of application No. 14/743,213, filed on Jun. 18, 2015, now Pat. No. 10,028,503.

(60) Provisional application No. 62/013,662, filed on Jun. 18, 2014.

(51) Int. Cl.
| C07D 241/40 | (2006.01) |
| A01N 1/02 | (2006.01) |
| C07D 209/04 | (2006.01) |

(52) U.S. Cl.
CPC .......... *A01N 1/0221* (2013.01); *A01N 1/0226* (2013.01); *C07D 209/04* (2013.01); *C07D 241/40* (2013.01)

(58) Field of Classification Search
CPC .......................... A01N 1/0211; C07D 241/40
See application file for complete search history.

(56) References Cited

U.S. PATENT DOCUMENTS

| 4,994,367 A | 2/1991 | Bode et al. |
| 5,141,851 A | 8/1992 | Brown et al. |
| 5,238,922 A | 8/1993 | Graham et al. |
| 5,420,245 A | 5/1995 | Brown et al. |
| 5,420,334 A | 5/1995 | Singh et al. |
| 5,436,128 A | 7/1995 | Harpold et al. |
| 5,447,922 A | 9/1995 | Lawrence et al. |
| 5,470,832 A | 11/1995 | Gibbs et al. |
| 5,482,954 A | 1/1996 | Kohn et al. |
| 5,510,510 A | 4/1996 | Patel et al. |
| 5,523,430 A | 6/1996 | Patel et al. |
| 5,567,841 A | 10/1996 | Magnin et al. |
| 5,574,025 A | 11/1996 | Anthony et al. |
| 5,602,098 A | 2/1997 | Sebti et al. |
| 5,618,964 A | 4/1997 | Cheng et al. |
| 5,629,302 A | 5/1997 | Eugster et al. |
| 5,631,401 A | 5/1997 | Stein et al. |
| 5,705,686 A | 1/1998 | Sebti et al. |
| 5,756,528 A | 5/1998 | Anthony et al. |
| 5,773,455 A | 6/1998 | Dong et al. |
| 5,786,193 A | 7/1998 | Greene et al. |
| 5,817,678 A | 10/1998 | Kim et al. |
| 5,830,868 A | 11/1998 | Bolton et al. |
| 5,834,434 A | 11/1998 | Sebti et al. |
| 5,843,941 A | 12/1998 | Marsters, Jr. et al. |
| 5,928,924 A | 7/1999 | Greene et al. |
| 5,929,077 A | 7/1999 | Leftheris |
| 6,011,029 A | 1/2000 | Ding et al. |
| 6,083,979 A | 7/2000 | Sebti et al. |
| 6,156,746 A | 12/2000 | Leftheris et al. |
| 6,166,067 A | 12/2000 | Kriimer et al. |
| 6,191,147 B1 | 2/2001 | Brown et al. |
| 6,194,438 B1 | 2/2001 | Yang et al. |
| 6,197,771 B1 | 3/2001 | Bigge et al. |
| 6,211,193 B1 | 4/2001 | Remiszewski et al. |
| 6,214,827 B1 | 4/2001 | Afonso et al. |
| 6,214,828 B1 | 4/2001 | Doll et al. |
| 6,218,401 B1 | 4/2001 | Afonso et al. |
| 6,225,322 B1 | 5/2001 | Cooper et al. |
| 6,228,856 B1 | 5/2001 | Njoroge et al. |
| 6,228,865 B1 | 5/2001 | Doll et al. |
| 6,239,140 B1 | 5/2001 | Cooper et al. |

(Continued)

FOREIGN PATENT DOCUMENTS

| EP | 2014651 | 1/2009 |
| GB | 1424359 | 2/1976 |

(Continued)

OTHER PUBLICATIONS

Levay et al., "NSC23766, a Widely Used Inhibitor of Rac1 Activation, Additionally Acts as a Competitive Antagonist at Muscarinic Acetylcholine Receptors," J Pharm and Exp Therap (Jul. 25, 2013) vol. 347, No. 1, pp. 69-79.

European Exam Report dated Dec. 3, 2019 for EP 15 895 847.0.

Flower et al., 2002, Drug design, cutting edge approaches, Royal Society of Chemistry, Cambridge, UK, pp. 21-27.

Akbar H., PhD., et a., "RhoA and Rac1 Gtpases Differentially Regulate Agonist-Receptor Mediated ROS Generation in Platelets," BLOOD, Dec. 6, 2014, 124(21 ), Abstract Only, 2 pgs.

Akbar, H., et al., "[43] Rational Design and Application of a RAC GTPase-Specific Small Molecule Inhibitor" Regulations and Effectors of Small GTPases: RHO Family; Methods in Enzymology, 2006, vol. 406, pp. 554-565, 6 pgs.

(Continued)

*Primary Examiner* — Rei Tsang Shiao
(74) *Attorney, Agent, or Firm* — Knobbe, Martens, Olson & Bear, LLP

(57) ABSTRACT

Disclosed are compositions and methods for slowing, preventing, or reversing platelet damage, particularly as may occur during blood banking or during refrigeration of platelets. The composition may include one or more of a RAC inhibitor, a CDC42 inhibitor, a RHOA inhibitor, or a combination thereof. The compositions may further include a pharmaceutically acceptable carrier.

29 Claims, 23 Drawing Sheets

(56) References Cited

U.S. PATENT DOCUMENTS

| | | |
|---|---|---|
| 6,242,433 B1 | 6/2001 | Balsamo et al. |
| 6,242,458 B1 | 6/2001 | Bishop et al. |
| 6,248,756 B1 | 6/2001 | Anthony et al. |
| 6,258,824 B1 | 7/2001 | Yang |
| 6,262,110 B1 | 7/2001 | Shaikenov et al. |
| 6,265,382 B1 | 7/2001 | Doherty et al. |
| 6,268,394 B1 | 7/2001 | Shaikenov et al. |
| 6,277,854 B1 | 8/2001 | Njoroge et al. |
| 6,294,552 B1 | 9/2001 | Lyssikatos et al. |
| 6,316,462 B1 | 11/2001 | Bishop et al. |
| 6,329,376 B1 | 12/2001 | Bergman |
| 6,387,905 B2 | 2/2002 | Njoroje et al. |
| 6,358,968 B1 | 3/2002 | Remiszewski et al. |
| 6,362,188 B1 | 3/2002 | Guzi et al. |
| 6,372,747 B1 | 4/2002 | Taveras et al. |
| 6,376,496 B1 | 4/2002 | Hartman et al. |
| 6,387,903 B1 | 5/2002 | Dinsmore et al. |
| 6,387,926 B1 | 5/2002 | Bhide et al. |
| 6,387,948 B1 | 5/2002 | Kwon et al. |
| 6,399,615 B1 | 6/2002 | Guzi et al. |
| 6,403,581 B1 | 6/2002 | Ayral-Kaloustain et al. |
| 6,410,541 B2 | 6/2002 | Remiszewski et al. |
| 6,423,751 B1 | 6/2002 | Liao |
| 6,426,352 B1 | 7/2002 | Njoroge et al. |
| 6,432,959 B1 | 8/2002 | Cooper et al. |
| 6,440,974 B2 | 8/2002 | Doll et al. |
| 6,440,989 B2 | 8/2002 | Afonso et al. |
| 6,441,017 B1 | 8/2002 | Bell et al. |
| 6,451,812 B1 | 9/2002 | End et al. |
| 6,458,783 B1 | 10/2002 | Ding et al. |
| 6,458,935 B1 | 10/2002 | Burns et al. |
| 6,492,381 B1 | 12/2002 | Bishop et al. |
| 6,495,564 B1 | 12/2002 | Lyssikatos et al. |
| 6,500,841 B1 | 12/2002 | Desolms et al. |
| 6,511,800 B1 | 1/2003 | Singh |
| 6,528,523 B2 | 3/2003 | Njoroge et al. |
| 6,535,820 B1 | 3/2003 | Stickland et al. |
| 6,539,309 B1 | 3/2003 | Stickland et al. |
| 6,545,020 B1 | 4/2003 | Van Ginckel et al. |
| 6,572,850 B1 | 6/2003 | Mandeville, III et al. |
| 6,576,639 B1 | 6/2003 | Doll et al. |
| 6,579,887 B2 | 6/2003 | Lyssikatos et al. |
| 6,586,447 B1 | 7/2003 | Lyssikatos et al. |
| 6,586,461 B1 | 7/2003 | Gibbs |
| 6,596,735 B1 | 7/2003 | Yang |
| 6,615,359 B2 | 9/2003 | Eyres et al. |
| 6,617,359 B2 | 9/2003 | Wohlfart et al. |
| 6,649,638 B1 | 11/2003 | Brown et al. |
| 7,122,570 B2 | 10/2006 | Koppitz et al. |
| 7,417,026 B2 | 8/2008 | Williams et al. |
| 7,517,890 B2 | 4/2009 | Zheng et al. |
| 7,612,080 B2 | 11/2009 | Zheng et al. |
| 7,826,982 B2 | 11/2010 | Zheng et al. |
| 8,383,124 B2 | 2/2013 | Zheng et al. |
| 10,028,503 B2 * | 7/2018 | Zheng .................. C07D 209/04 |
| 10,405,538 B2 * | 9/2019 | Zheng .................. C07D 209/04 |
| 2004/0137518 A1 | 7/2004 | Lambert et al. |
| 2005/0049294 A1 | 3/2005 | Palladino et al. |
| 2005/0069553 A1 | 3/2005 | Zheng et al. |
| 2005/0238666 A1 | 10/2005 | Williams et al. |
| 2006/0135542 A1 | 6/2006 | Zheng et al. |
| 2009/0041737 A1 | 2/2009 | Maurer et al. |
| 2013/0202553 A1 | 8/2013 | Zheng |
| 2015/0366182 A1 | 12/2015 | Zheng et al. |
| 2018/0139952 A1 | 5/2018 | Zheng et al. |

FOREIGN PATENT DOCUMENTS

| | | |
|---|---|---|
| WO | WO 2004/076445 | 9/2004 |
| WO | WO 2005/017160 | 2/2005 |
| WO | WO 2005/037791 | 4/2005 |
| WO | WO 2005/051392 | 6/2005 |
| WO | WO 2006/055833 A3 | 5/2006 |
| WO | WO 2009/114725 | 9/2009 |
| WO | WO 2013/166043 | 11/2013 |
| WO | WO 14/120683 | 8/2014 |
| WO | WO 2016/204809 | 12/2016 |

OTHER PUBLICATIONS

Akbar, H., et al., "Abstract 58: Differential Signaling by CRP-PACI-NOXI and Thrombin-Pac I-NOX2 Axes Regulates Ros Generation and Platelet Activation," American Heart Association; Oral Abstract Presentations; Session Title: Concurrent Session IV B: 1 Platelet Production, Signaling and Function, Arteriosclerosis, Thrombosis, and Vasular Biology, 2015, 35:A58, 1 pg.

Akbar, H., et al., "Gene Targeting Implicates Cdc42 GTPase in GPVI and Non-GPVI Mediated Platelet Filopodia Formation, Secretion and Aggregation," PLoS ONE, Jul. 2011, 6(7):e22117, 9 pgs.

Akbar, H., et al., "Genetic and pharmacologic evidence that Rac1 GTPase is involved in regulation of platelet secretion and aggregation," Journal of Thrombosis and Haemostasis, 2007, 5:1747-1755, 9 pgs.

Akbar, H., et al., "Rac2 GTPase plays a critical role in platelet adhesion as well as in sustenance and perpetuation of platelet aggregation," Blood, (ASH Annual Meeting Abstracts), 2004, 104:Abstract 3523, 1 pg.

Arikawa, K., et al., "Ligand-dependant inhibition of B16 melanoma cell migration and invasion via endogenous S1P2 G protein-coupled receptor. Requirement of inhibition of cellular RAC activity," J Biol Chem, Aug. 29, 2003, 278(35):23841-51, 12 pgs.

Aslan, J.E., et al., "Rho GTPases in platelet function," Journal of Thrombosis and Haemostasis, 2012, 11:35-46, 12 pgs.

Aubuchon, MD, J.P., et al., "Comparison of computerized formulae for determination of platelet recovery and survival," Letter to the Editor, Transfusion, Jul. 2005, vol. 45, pp. 1237-1238, 2 pgs.

Bastola, D.R., et al., "Downregulation of PTEN/MMAC/TEP1 expression in human prostate cancer cell line DU145 by growth stilului," Mol. Cell Biochem., 2002, 236:75-81, 8 pgs.

Behnke, MD, O., "Effects of Some Chemicals on Blood Platelet Microtubules, Platelet Shape and Some Platelet Functions in vitro," Scand. J. Haemat., 1970, 7:123-140, 18 pgs.

Blan, A.D., et al., "Evidence of platelet activation in hypertension," J Hum Hypertens, 1997, 11:607-609, 3 pgs.

Broijersen, A., et al., "Platelet activity In Vivo in hyperlipoproteinemia—Importance of combined hyperlipidemia," Thromb Haemost, 2001,79:268-275, 8 pgs.

Cancelas, J.A., et al., "Rac GTPases differentially integrate signals regulating hemotopoietic stem cell localization," Nature Medicine, Aug. 2005, 11(8):886-891, 6 pgs.

Chuang, T.-H., et al., "Abr and Bcr are multifunctional regulators of the Rho GTP-binding protein family," Proc. Natl. Acad. Sci. USA, Biochemistry, Oct. 1995, 92:10202-10286, 5 pgs.

Clark, R.D., et al., "Consensus scoring for ligand/protein interactions," J Mol Graph Model, 2002, 20:281-295, 15 pgs.

De Jong, R., et al., "Crkl is Complexed with Tyrosine-phosphorylated Cbl in Ph-positive Leukemia," The Journal of Biological Chemistry, Sep. 15, 1995, 270(37):21468-21471, 5 pgs.

De Jong, R., et al., "Tyrosine phosphorylation of murine Crkl," Oncogene, 1995, 11:1469-1474, 6 pgs.

Deininger, et al., "Review article: The molecular biology of chronic myeloid leukemia," Blood, 96(10):3343-3356, 15 pgs.

Del Pozo, M.A., et al., "Adhesion to the extracellular matrix regulates the coupling of the small GTPase Rac to its effector PAK," EMBO J., 2000, 19:2008-2014, 7 pgs.

Delaney, M.K., et al., "The Role of Rac1 in Glycoprotein Ib-IX-Mediated Signal Transduction and Integrin Activation," Areriosclerd Thromb Vasc Biol, Nov. 2012, 32:2761-2768, 8 pgs.

Dumont, L.J., et al., "A randomized controlled trial evaluating recovery and survival of 6% dimethly sulfozide-frozen autologous platelets in healthy volunteers," Transfusion, Jan. 2013, 53:128-137, 10 pgs.

Dumont, L.J., et al., "Invitro and in vivo quality of leukoreduced apheresis platelets stored in a new platelet additive solution," Transfusion, May 2013, 53:972-980, 9 pgs.

(56) References Cited

OTHER PUBLICATIONS

Dunbrack, Jr., et al., "Bayesian statistical analysis of protein side-chain rotamer preferences," Protein Science, 1997, 6:1661-1681, 21 pgs.
Eder, A.F., et al., "Bacterial screening of apheresis platelets and the residual risk of septic transfusion reactions: the American Red Cross experience (2004-2006)", Transfusion, Jul. 2007, 47:1134-1142, 9 pgs.
Engers, R., et al., "Tiam1 mutations in human renal-cell carcinomas," Int J Cancer, 2000, 88:369-376, 8 pgs.
Etienne-Manneville, S., et al., "Rho GTPases in Cell Biology," Nature, Dec. 2002, 420:629-635, 7 pgs.
Falet, H., et al., "Platelet-associated IgAs and impaired GPVI responses in platelets lacking WIP," Blood, Nov. 19, 2009, 114(21):4729-4737, 9 pgs.
Fiegen, et al., "Alternative splicing of Rac1 generates Rac1b, a Self-activating GTPase," J Biol Chem, Feb. 6, 2004, 29(6):4743-4749, 8 pgs.
Fioretos, T., et al., "Regional Localization and Developmental Expression of the BCR Gene in Rodent Brain," Cell Mol Biol Res., 1995, 41(2):97-102, 10 pgs.
Fioretos, T., et al., "Standpoint on imprinting of BCR and ABL," Leukemia, 1995, 9(4):743-44, 3 pgs.
Fitzgerald, MB, D.J., et al., "Platelet activation in unstable coronary disease," N Engl J Med., 1996, 315:983-989, 7 pgs.
Florian, M.C., et al., "CDC42 Activity Regulates Hematopoietic Stem Cell Aging and Rejuvenation," Cell Stem Cell., May 4, 2012, 10(5):520-530, 22 pgs.
Flyvbjerg, A., et al., "Stimulation of hepatic insulin-like growth factor-binding protein-1 and -3 gene expression by octreotide in rats," Journal of Endrocrinology, 1995, 147:545-551, 7 pgs.
Fontaine, M.J., et al., "Improving platelet supply chains through collaborations between blood centers and transfusion services," Transfusion, Oct. 2009, 49:2040-2047, 8 pgs.
Fritz, G., et al., "Rho GTPases are over-expressed in human tumors," Int J Cancer, 1999, 81:682-687, 6 pgs.
Fuller, A.K., et al., "Bacterial culture reduces but does not eliminate the risk of septic transfusion reactions to single-donor platelets," Transfusion, Dec. 2009, 49:2588-2593, 6 pgs.
Gao, Y., et al., "Rational design and characterization of a RAC GTPase-specific small molecule inhibitor," PNAS, May 18, 2004, 101(20):7618-7623, 6 pgs.
Gao, Y., et al., "Trp56 of Rac1 Specifies Interaction with a Subset of Guanine Nucleotide Exchange Factors," J Biol Chem, 2001, 276:47530-47541, 14 pgs.
Gawaz, M., "Role of platelets in coronary thrombosis and reperfusion of ischemic myocardium," Cardiovas. Res., 2004, 61:498-511, 14 pgs.
Goodford, P.J., "A Computational Procedure for Determining Energetically Favorable Binding Sites on Biologically Important Macromolecules," J Med Chem, 1985, 28:849-857, 9 pgs.
Grizot, et al., "Crystal Structure of the Rac1-RhoGDI Complex Involved in NADPH Oxidase Activation," Biochemistry, 2001, 40:10007-10013, 7 pgs.
Groffen, Ph.D., J., "Two candidate breast cancer genes on chromosome," Childrens Hospital, Los Angeles, 1995, 1 pg.
Gruneberg, S., et al., "Subnanomolar Inhibitors from Computer Screening: A Model Study Using Human Carbonic Anhydrase II," Chem Int Ed Engl., 2001,40:389-393, 5 pgs.
Gu, Y., et al., "Hematopoietic Cell Regulation by Rac1 and Rac2 Guanosine Triphosphatases," Science, 2003, 302:445-449, 6 pgs.
Guo, F., et al., "P19Arf-p53 Tumor Suppressor Pathway Regulates Cell Motility by Suppression of Phosphoinositide 3-Kinase and Rac1 GTPase Activities," J Biol Chem, 2003, 278(16):14414-14419, 7 pgs.
Guyatt, G., et al., "Grades of Recommendation for Antithrombotic Agents," Chest, 2001, 119:3S-7S, 5 pgs.
Haataja, L., et al., "Characterization of Rac3, a Novel Member of the Pho Family," The Journal of Biological Chemistry, Aug. 15, 1997, 272(33):20384-20388, 6 pgs.
Haataja, L., et al., "Deletion within the D17S34 Locus in a Primitive Neuroectodermal Tumor," Cancer Research, Jan. 1, 1997, 57:32-34, 3 pgs.
Hartwig, J.H., "Mechanisms of Actin Rearrangements Mediating Platelet Activation," The Journal of Cell Biology, Sep. 1992, 118(6):1421-1442, 22 pgs.
Haszon, I, et al., "Platelet aggregation, blood viscosity and serum lipids in hypertensive and obese children," Eur J Pediatr, 2003, 162:385-390, 7 pgs.
Hawkins, P.T., et al., "PDGF stimulates an increase in GTP-Rac via activation of phosphoinostitide 3-kinase," Curr Biol, 1995, 5:393-403, 11 pgs.
Heeschen, M.D., C., et al., "Soluble CD40 Ligand in Acute Coronary Syndromes," N Engl J Med, 2003, 348:1104-1111, 8 pgs.
Heisterkamp, N., et al., "Localization of the Human Mitochondrial Citrate Transporter Protein Gene to Chromosome 22Q11 in the DiGeorge Syndrome Critical Region," Geonomics, 1995, 29:451-456, 6 pgs.
Hoffmeister, K.M., et al., "Glycosylation Restores Survival of Chilled Blood Platelets," Science, Sep. 12, 2003, 301:1531-1534, 5 pgs.
Hoffmeister, K.M., et al., "Mechanisms of Cold-induced Platelet Actin Assembly," The Journal of Biological Chemistry, Jul. 6, 2001, 276(27):24751-24759, 10 pgs.
Hoffmeister, K.M., et al., "The Clearance Mechanism of Chilled Blood Platelets," Cell, Jan. 10, 2003, 112:87-97, 11 pgs.
Hoffmeister, M., et al., "Cyclic Nucleotide-dependant Protein Kinases Inhibit Binding of 14-3-3 to the GTPase-activating Protein Rap1GAP2 in Platelets," The Journal of Biological Chemistry, Jan. 25, 2008, 283(4):2297-2306, 11 pgs.
Hornsey, V.S., et al., "Extended storage of platelets in SSP+ platelet additive solution," Vox Sanguinis, 2006, 91:41-46, 6 pgs.
Huo, T., et al., "Role of Platelets in the Development of Atherosclerosis," Trends Cardiovasc Med, 2004, 14:18-22, 5 pgs.
Hurst, T., "Flexible 3D Searching: The Directed Tweak Technique," J Chem Inf Comput Sci, 1994, 34:190-196, 7 pgs.
Jacobs, M.R., et al., "Detection of bacterial contamination in prestorage culture-negative apheresis platelets on day of issue with the Pan Genera Detection test," Transfusion, Dec. 2011, 51:2573-2582, 10 pgs.
Kaartinen, V., et al., "Abnormal lung development and cleft palate in mice lacking TGF-B3 indicates defects of epithelial-mesenchymal interaction," Nature Genetics, Dec. 1995, 11:415-421, 7 pgs.
Kaempchen, K., et al., "Upregulation of the Rac1/JNK signaling pathway in primary human schwannoma cells,"Hum Mol Genet, 2003, 12(11):1211-1221, 11 pgs.
Kaighn, M.E., et al., "Establishment and characterization of human prostatic carcinoma cell line (PC-3)," Invest Urol, 1979, 17(1):16-23, abstract only, 2 pgs.
Kamai, T., et al., "Overexpression of RhoA mRNA is associated with advanced stage in testicular germ cell tumor," BJU Int., 2001, 87:227-231, 5 pgs.
Karnoub, et al., "Molecular basis for Rac1 recognition by guanine nucleotide exchange factors." Nat Struct Biol. 2001. 8:1037-1041. 5 pgs.
Kato-Stankiewicz, J., et al., "Inhibitors of Ras/Raf-1 interaction identified by two-hybrid screening revert Ras-dependant transformation phenotypes in human cancer cells," PNAS, 2002, 99(22):14398-14403, 6 pgs.
Kawano, Y., et al., "Smooth Muscle Contraction by Small GTPase Rho," Nagoya J. Med. Sci., 2002, 65:1-8, 8 pgs.
Khosravi-Far, et al., "Activation of Rac1, RhoA, and Mitogen-Activated Protein Kinases Is Required for Ras Transformation," Mol Cell Biol, 1995, 15:6453, 11 pgs.
Lang, S.H., et al., "Enhanced Expression of Vimentin in Motile Prostate Cell Lines and in Poorly Differentiated and Metastasis Prostate Carcinoma," Prostate, 2002, 52:253-263, 11 pgs.
Liliental, J., et al., "Genetic deletion of the Pten tumor suppressor gene promotes cell motility by activation of Rac1 and Cdc42 GTPases," Curr Bio, 2000, 10:401-404, 4 pgs.

(56) References Cited

OTHER PUBLICATIONS

Liu, et al., "Mobilization of Hematopoitic Stem/Progenitor Cells by a Cdc42 Activity-Specific Inhibitor," 2008 ASH Annual Meeting Abstracts, Abstract 68, 112(11):32-33, 2 pgs.

Macherla, V.R., et al., "Structure—Activity Relationship Studies of Salinospotamide A (NPI-0052), a Novel Marine Derived Proteasome Inhibitor," J Med Chem., 2005, 48:3684-3687, 4 pgs.

Manduteanu, I, et al., "Increased adhesion of human diabetic platelets to cultured valvular endothelial cells," J Submicrosc Cytol Pathol, 1992, 24(4):539-547, 9 pgs.

Martens, J.W.M., et al., "Characterization of Baculovirus Insecticides Expressing Tailored Bacillus thuringiensis CrylA(b) Crystal Proteins," Journal of Invertebrate Pathology, 1995, 66:249-257, 9 pgs.

McDonald, C.P., et al., "Evaluation of donor arm disinfection techniques," Vox Sanguinis, 2001, 80:135-141, 7 pgs.

McDonald, C.P., et al., "Relative values of the interventions of diversion and improved donor-arm disinfection to reduce the bacterial risk from blood transfusion," Vox Sanguinis, 2004, 86:178-182, 5 pgs.

McDonlad, C.P., et al., "Evaluation of the 3D BacT/Alert automated system for the detection of microbial contamination of platelet concentrates," Transfusion Medicine, 2002, 12:303-309, 8 pgs.

McDonlad, C.P., et al., "Pall eBDS: an enhanced bacterial detection system for screening platelet concentrates," Transfusion Medicine, 2005, 15:259-268, 10 pgs.

Mira, J.P., et al., "Endogenous, hyperactive Rac3 controls proliferation of breast cancer cells by a p21-activated kinase-dependent pathway," PNAS, 2000, 97:185-189, 5 pgs.

Mononen, I., et al., "Recombinant glycosylasparaginase and in vitro correction of aspartylglycosaminuria," The FASEB Journal, Mar. 1995, 9:428-433, 6 pgs.

Morris, C., et al., "Spatial organization of ABR and CRK genes on human chromosome band 17p13.3," Oncogene, 1995, 10:1009-1011, 3 pgs.

Movilla, N., et al., "How Vav proteins discriminate the GTPases Rac1 and RhoA from Cdc42," Oncogene, 2001, 20:8057-8065, 9 pgs.

Murphy, MD, S., et al., "Platelet Preservation: Effect of Storage Temperature on Maintenance of Platelet Visibility—Deleterious Effect of Refrigerated Storage," The New England Journal of Medicine, May 15, 1969, 280(20):1094-1098, 6 pgs.

Narumiya, S., et al., "rho Gene Products, Botulinum C3 Exoenzyme and Cell Adhesion," Cell Signal, 1993, 5:9-19, 11 pgs.

Nassar, N., et al., "Structure-Function Based Design of Small Molecule Inhibitors Targeting Pho Family GTPases," Current Topics in Medicinal Chemistry, 2006, 6:1109-1116, 8 pgs.

Nityanand, S., et al., "Platelets in Essential Hypertension," Thromb Res, 1993, 72:447-454, 8 pgs.

Norman, P., "Cutting Edge Approaches to Drug Design," Idrugs, 2001, 4(6):659-661, 3 pgs.

Nur-E-Kamal, et al., "The CDC42-specific inhibitor derived from ACK-1 blocks v-Ha-Ras-induced transformation," Oncogene, 1999, 18:7787-7793, 7 pgs.

Pelish, et al., "The Cdc42 inhibitor secramine B prevents cAMP-induced K+ conductance in intestinal epithelial cells," Biochemical Pharmacology, 2006, 71:1720-1726, 13 pgs.

Perola, E., et al., "Successful Virtual Screening of a Chemical Database for Farnesyltransferase Inhibitor Leads," J Med Chem, 2000, 43:401-408, 8 pgs.

Preston, R.A., et al., "Effects of Severe Hypertension on Endothelial and Platelet Microparticles," Hypertension, 2003, 41:211-217, 8 pgs.

Qiu, et al., "Cdc42 Regulates Anchorage-Independent Growth and is Necessary for Ras Transformation," Mol Cell Biol, 1997, 17:3449-3458, 10 pgs.

Rarey, et al., "A Fast Flexible Docking Method using an Incremental Construction Algorithm," J Mol Biol, 1996, 261:470-489, 20 pgs.

Ridley, A., et al., "The Small OTP-Binding Protein rac Regulates Growth Factor-Induced Membrane Ruffling," Cell, 1992, 70:401-410, 10 pgs.

Roberts, A.W., et al., "Deficiency of the Hematopoietic Cell-Specific Rho Family GTPase Rac2 Is Characterized by Abnormalities in Neutrophil Function and Host Defense," Immunity, 1999, 10:183-196, 14 pgs.

Rumjantseva, V., et al., "Dual roles for hepatic lectin receptors in the clearance of chilled platelets," Nature Medicine, Nov. 2009, 15(11):1273-1280, 9 pgs.

Sahai, E., et al., "Differing modes of tumor cell invasion have distinct requirements for Rho/ROCK signalling and extracellular proteolysis," Nat Cell Biol, Aug. 2003, 5(8):711-719, 12 pgs.

Sahai, E., et al., "Rho-GTPases and Cancer," Nature Reviews Cancer, 2002, 2:133-142, 13 pgs.

Schmidt, A., et al., "Guanine nucleotide exchange factors for Rho GTPases: turning on the switch," Genes Dev., 2002, 16:1587-1609, 24 pgs.

Schmitz, A.A., et al., "Rho GTPases: Signaling, Migration, and Invasion," Exp Cell Res, 2000, 261: 1-12, 12 pgs.

Schnelzer, A., et al., "Rac 1 in human breast cancer: overexpression, mutation analysis, and characterization of a new isoform, Rac1b," Oncogene, 2000, 19:3012-3020, 8 pgs.

Sekine, A., et al., "Asparagine Residue in the rho Gene Product Is the Modification Site for Botulinum ADP-ribosyltransferase," J Biol Chem., 1989, 264:8602-8605, 4 pgs.

Serebruany, V.L. et al., "Increased soluble platelet/endothelial cellular adhesion molecule-1 and osteonectin levels in patients with severe congestive heart failure. Independence of disease etiology, and antecendent aspirin therapy," Eur J Heart Failure, 1999, 1:243-249, 7 pgs.

Shang, X., et al., "Chapter 3: Rational Design of Rho GTPase-Targeting Inhibitors," Rational Drug Design: Methods and Protocols, Methods in Molecular Biology, 2012, 928:29-38, 10 pgs.

Shang, X., et al., "Rational Design of Small Molecule Inhibitors Targeting RhoA subfamily Rho GTPases," Chemistry & Biology, Jun. 22, 2012, 19(6):699-710, 12 pgs.

Shang, X., et al., "Rational Design of Small Molecule Inhibitors Targeting RhoA subfamily Rho GTPases," Chem Biol, Jun. 22, 2012, 19(6):699-710, 20 pgs.

Silver, Ph.D., P.A., "Genome-Wide Nucleic Acid/Protein Interaction in Breast Cancer," Dana-Farber Cancer Institute, May 2004, 14 pgs.

Skorski, T., et al., "BCR/ABL-mediated leukemogenesis requires the activity of the small GTP-binding protein Rac," PNAS, 1998, 95(20):11858-11862, 5 pgs.

Sorof, J., et al., "Obesity Hypertension in Children, A Problem of Epidemic Proportions," Hypertension, 2002, 40:441-447, 8 pgs.

Stepan, V.M., et al., "Gastrin induces c-fos gene transcription via multiple signaling pathways," Am J Physiol, 1999, 276:G415-G424, 10 pgs.

Suwa, H., et al., "Overexpression of the rhoC gene correlates with the progression of ductal adenocarcinoma of the pancreas," Br J Cancer, 1998, 77:147-152, 6 pgs.

Symons, M., "Adhesion signaling: PAK meets Rac on solid ground," Curr Biol, 2000, 10:R535-R537, 3 pgs.

The SALT Collaborative Group, "Swedish Aspirin Low Dose Trial (SALT) of 75 mg aspirin as secondary prophylaxis after cerebrovascular ischemic events," Lancet, 1991, 338:1345-1349, 5 pgs.

Townsend, L., "Extended platelet storage makes a welcome difference," Medical Laboratory Observer, Jun. 2007, 39(6):40-41, 6 pgs.

Tschoepe, D., et al., "Platelets in Diabetes: the role in Hemostatic Regulation in Atherosclerosis," Semin Thromb Hemost, 1993, 19(2):122-128, 7 pgs.

Valeri, C.R., et al., "Effect of thrombopoietin alone and a combination of cytochalasin B and ethylene glycol bis(B-aminoethyl ether) N,N'-tetraacetic acid-AM on the survival and function of autologous baboon platelets stored at 4° C. for as long as 5 days," Transfusion, Jun. 2004, 44:865-870, 6 pgs.

Van Aelst, L., et al., "Rho GTPases and signaling networks," Genes Dev, 1997, 11:2295-2322, 28 pgs.

(56) References Cited

OTHER PUBLICATIONS

Voncken, J.W., et al., "BCR/ABL P210 and P190 Cause Distinct Leukemia in Transgenic Mice," Blood, Dec. 15, 1995, 86(12):4603-4611, 9 pgs.
Voncken, J.W., et al., "Increased Neutrophil Respiratory Burst in bcr-Null Mutants," Cell, Mar. 10, 1995, 80:719-728, 10 pgs.
Wang, L., et al., "Cell type-specific functions of Rho GTPases revealed by gene targeting in mice," Trends in Cell Biology (2006), 17(2):58-64, 7 pgs.
Waszkowycz, B., Large-scale virtual screening for discovering leads in the postgenomic era, IBM Systems J, 2001, 40:360-376, 17 pgs.
Weber, C.F., et al., "Pathogen-Reduction for Platelet Concentrates," Clin. Lab., 2011, 57:293-295, 3 pgs.
White, MD, J.G., "Influence of Taxol on the Response of Platelets to Chilling," Taxol, 1982, 108(2):184-195, 12 pgs.
White, MD, J.G., "Effects of Colchicine and Vinca Alkaloids on Human Platelets," Platelet Contractility, Aug. 1968, 53(2): 281-291, 11 pgs.
Winocour, P.D., "Platelet Abnormalities in Diabetes Mellitus," Diabetes, 1992, 41(Suppl 2):26-31, 7 pgs.
Winokur, R., et al., "Mechanism of Shape Change in Chilled Human Platelets," Blood, Apr. 1, 1995, 85(7):1796-1804, 10 pgs.
Worthylake, D.K., et al., "Crystal structure of Rac1 in complex with the quinine nucleotide exchange region of Tiam1," Nature, 2000, 408:682-688, 7 pgs.
Xu, F., et al., "Temperature cycling improves in vivo recovery of cold-stored human platelets in a mouse model of transfusion," Transfusion, Jun. 2013, 53:1178-1186, 9 pgs.
Yang, et al., "Pho GTPase Cdc42 coordinates hematopoietic stem cell quiescence niche interaction in the bone marrow," PNAS, 2007, 104(12):5091-5096, 6 pgs.
Zhao, J.J., et al., "Human mammary epithelial cell transformation through the activation of phosphatidylinositol 3-kinase," Cancer Cell, May 2003, 3(5):483-495, 13 pgs.
Zheng, Y., "Dbl family guanine nucleotide exchange factors," Trends Biochem Sci, 2001, 26:724-732, 9 pgs.
Zheng, Y., et al., "Direct Involvement of the Small GTP-binding Protein Rho in Ibc Oncogene Function," J Biol Chem, 1995, 270:9031-9034, 4 pgs.
Zhou, X., et al., "Cell Type-specific Signaling Function of RhoA GTPase: Lessons from Mouse Gene Targeting," The Journal of Biological Chemistry, (2013), 288(51):36179-36188, 10 pgs.
U.S. Appl. No. 60/523,599, filed Nov. 20, 2003.
U.S. Appl. No. 60/629,380, filed Nov. 19, 2004.
U.S. Appl. No. 60/703,587, filed Jul. 29, 2005.
International Search Report and Written Opinion dated Apr. 5, 2005 for Application No. PCT/US2004/039090.
International Search Report and Written Opinion dated Jun. 27, 2006 for Application No. PCT/US2005/041949.
International Search Report and Written Opinion dated Nov. 26, 2009 for Application No. PCT/US2009/037013.
International Search Report and Written Opinion dated Mar. 7, 2016 for Application No. PCT/US2015/066252.
Akbar et al., Sep. 28, 2016, RhoA and Rac1 GTPases differentially regulate agonist-receptor mediated reactive oxygen species generation in platelets, PLoS One, 11(9):e0163227.doi:10.1371/journal.pone.0163227.
Antinarelli et al., 2015, 4-aminoquinoline derivatives as potential antileishmanial agents, Chemical biology & drug design, 86(4):704-714.
Cancelas, Jun. 19, 2018, Future of platelet formulations and storage, RDCR Symposium Thor group, Bergen, Norway, 40 pp.
Chemical Abstract compound, STNext. RN 92856-78-5(Entered STN: Dec. 17, 1984), 1 p.
Chemical Abstract compounds, STNext. RN 924202-68-6 (Entered STN: Mar. 1, 2007), RN 727980-43-0 (Entered STN: Aug. 18, 2004), 1 p.
Chemical Abstract compounds, STNext. RN 920646-81-7 (Entered STN: Feb. 13, 2007), RN 1814906-80-3 (Entered STN: Oct. 26, 2015), RN 1448458-25-0 (Entered STN: Aug. 15, 2013), RN 949563-10-4 (Entered STN: Oct. 7, 2007), RN 949563-09-1 (Entered STN: Oct. 7, 2007), RN 930729-10-5 (Entered STN: Apr. 18, 2007), 3 pp.
The Royal Children's Hospital Melbourne, Nov. 3, 2012, Platelet transfusion, https://web.archive.org/web/20121103004450/https://www.rch.org.au/bloodtrans/about_blood_products/Platelet_transfusion/.

\* cited by examiner

Rho GTPase Inhibitors

| COMPOUNDS | | TARGET |
|---|---|---|
|  | NSC23766 | RAC |
|  | CASIN | CDC42 |
|  | G04 | RHOA |

0 µM NSC23766    50 µM NSC23766

PLATELET STORAGE METHODS AND COMPOSITIONS FOR SAME

CROSS REFERENCE TO RELATED APPLICATIONS

This application is a continuation of U.S. application Ser. No. 14/743,213, filed Jun. 18, 2015, of the same title, which claims priority to and benefit of U.S. Provisional Application Ser. No. 62/013,662, filed Jun. 18, 2014, of same title, in their entirety for all purposes.

BACKGROUND

Patients with low platelet counts often require platelet transfusion. This is particularly crucial in the treatment of patients with cancer or massive trauma. The use of platelet transfusions has increased dramatically since 1980s, but a safe, long-term platelet storage method remains unavailable. The demonstration of successful, refrigerated storage of platelets for extended lengths of time, for example, 7 days or longer, would dramatically change the current practice of platelet transfusion in the Western World. Approximately 3,000,000 doses of platelets are used in the United States every year, and account for sales of ~$1.5 Billion annually. The current short shelf-life represents a major handicap to convert platelet products into effective commodities. Depending on the time of the year, month or even week, up to 20% of products can be wasted due to expiration. In the meantime, there are moments of platelets shortages due to unpredictable increased usage. The extension of platelet product shelf-life would strengthen the national inventory of platelets for oncological and trauma patients. An estimated 10-fold increase in the need of platelet and plasma products is expected by the US government in war casualties and massive trauma patients due to the 1 red cell: 1 platelet: 1 plasma product transfusion policy.

Current practice has platelets stored at 20 to 24° C. after preparation, which has a limited lifetime up to 5 days, primarily due to concerns about bacterial contamination. Bacterial contamination of platelet products for transfusion is a major safety problem in blood banking. The consequence of transfusion of contaminated products is increased morbi-mortality among a susceptible population of cancer patients (1). Different technologies have been developed aiming to minimize the risk of bacterial contamination including diversion pouches for collection, bacterial detection with automatic culture systems and pathogen reduction systems (2-6). While there has been a significant reduction in the number of cases of platelet transfusion associated sepsis, the risk of transfusion-associated sepsis ranges between 1 in 15,000 to 86,000 platelet transfusions (7, 8). Storage of platelets in cold temperatures, as is done for red cells, would reduce the proliferation of most bacteria and allow a longer period of storage (9), minimizing the current shortages (10) that the short storage time (5-day) for platelets approved by the FDA (11). Conventional cold storage of platelets, however, has been hampered by the discovery that the 24-hour recovery of chilled platelets was significantly reduced (14).

The development of a method to prevent platelet damage upon refrigeration is a much needed, and long sought after advance in blood banking. Such development would revolutionize the current method of platelet storage. The instant disclosure solves one or more of these deficiencies in the art.

BRIEF SUMMARY

Disclosed are compositions and methods for one or more of slowing, preventing, or reversing platelet damage, particularly as may occur during blood banking or during refrigeration of platelets. The composition may include one or more of a RAC inhibitor, a CDC42 inhibitor, a RHOA inhibitor, or a combination thereof. The compositions may further include a pharmaceutically acceptable carrier.

BRIEF DESCRIPTION OF THE DRAWINGS

FIG. 1A. Cold causes the actomyosin changes, Ca2+ mobilization, loss of spectrin anchorage, and Gplb clustering.

FIG. 1B. "Cold receptor" may stimulate Cdc42, Rac, and/or Rho activation, which in turn control lipid raft assembly and actomyesin reorganization, resulting in Gplb clustering.

FIG. 3A. Docking model of Casin bound to a Cdc42 surface groove required for activation.

FIG. 3B. Collagen-induced Cdc42 activation is inhibited by Casin (10 µM) in a GST-PAK pulldown assay.

FIG. 3C. Fibrinogen mediated platelet actin filopedia structure is blocked by Casin (10 µM). Rhodamine conjugated phalloidin-staining of platelets adhered to coated collagen surface.

FIG. 3D. Collagen induced aggregation is blocked by 10 µM Casin (upper panel) and is reversible (up to 30 µM Casin) upon a wash of the inhibitor treated platelets (lower panel).

FIG. 4A. X-ray structure of NSC23766 bound to a Rac 1 surface groove required for GEF activation.

FIG. 4B. Rac 1 activity is inhibited by NSC23 766 (50 µM) in a GST-PAK pulldown assay.

FIG. 4C. Fibrinogen-mediated platelet actin lamellopodia structure is blocked by NSC23 766 (50 µM). Rhodamine conjugated phalloidin-staining of platelets adhered to coated collagen surface.

FIG. 4D. Collagen induced aggregation is blocked by NSC23766 in a dose-dependent fashion.

FIG. 4E. Inhibition of collagen induced platelet aggregation by NSC23766 (50 µM) is reversible upon a wash of the inhibitor treated platelets.

FIG. 5A. Docking model of G04 bound to a RhoA surface groove required for GEF activation. Upper panel: low resolution; Lower panel: high resolution binding domain.

FIG. 5B. Collagen-induced RhoA activity is inhibited by Go4 (50 µM) in a GST-Rhotekin pulldown assay.

FIG. 5C. U46629 (10 mM/Fibrinogen (3 µM)-mediated platelet actin lamellopodia structure is blocked by G04 (30 µM). Rhodamine conjugated phalloidin-staining of platelets adhered to coated collagen surface.

FIG. 5D. Collagen induced aggregation is inhibited by G04 (upper panel). Similar to collagen, thrombin induced aggregation (data not shown) is blocked by G04 in a dose-dependent fashion (upper panel) and is reversible upon a wash of the inhibitor treated platelets (lower panel).

FIG. 6A. Experimental designs.

FIG. 6B-FIG. 6D. 24-hour recovery and survival of platelets in different conditions.

FIG. 6B. 24-hour recovery.

FIG. 6C-FIG. 6D. Platelet recovery at different time points. Donor platelets were stored at room temperature (squares) or pretreated with a mixed Rho GTPase inhibitors (50 μM NSC23766, 10 μM CASIN and/or 75 μM G04) or no drug (control). Data are presented as mean SD. *p<0.01 (Anova test with Bonferroni correction, between refrigerated with no inhibitor and refrigerated with triple inhibitor combination).

DETAILED DESCRIPTION

Figure 1A:
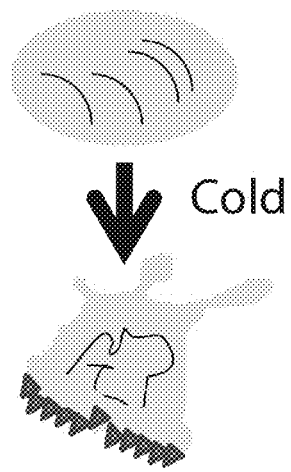
FIGS. 1A-1B depict a schematic model of "cold receptor" initiated intracellular events involving Rho GTPases.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are expressly incorporated by reference in their entireties.

Definitions

It must be noted that as used herein and in the appended claims, the singular forms "a," "an," and "the" include plural referents unless the context clearly dictates otherwise. Thus, for example, reference to "a platelet" includes a plurality of such platelets and reference to "the carrier" includes reference to one or more carriers and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Where particular values are described in the application and claims, unless otherwise stated the term "about" meaning within an acceptable error range for the particular value should be assumed.

An "amide" is a chemical moiety with formula —(R)n-C(O)NHR' or —(R)n-NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds of the invention may be designated as "C1-C4 alkyl" or similar designations. By way of example only, "C1-C4 alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

The term "ester" refers to a chemical moiety with formula —(R)n-COOR', where R and R' are independently selected from the group consisting of alkyl, cycloalkyl, aryl, heteroaryl (bonded through a ring carbon) and heteroalicyclic (bonded through a ring carbon), and where n is 0 or 1.

The substituent "R" appearing by itself and without a number designation refers to a substituent selected from the group consisting of hydrogen, alkyl, cycloalkyl, aryl, heteroaryl (bonded through a ring carbon) and heteroalicyclic (bonded through a ring carbon).

An "O-carboxy" group refers to a RC(=O)O— group, where R is as defined herein.

A "C-carboxy" group refers to a —C(=O)OR groups where R is as defined herein.

An "acetyl" group refers to a —C(=O)CH3, group.

A "trihalomethanesulfonyl" group refers to a X3CS(=O)2-group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)2NR, group, with R as defined herein.

A "N-sulfonamido" group refers to a RS(=O)2NH— group with R as defined herein.

A "trihalomethanesulfonamido" group refers to a X3CS(=O)2NR— group with X and R as defined herein.

An "O-carbamyl" group refers to a —OC(=O)—N(R)2, group—with R as defined herein.

An "N-carbamyl" group refers to a ROC(=O)NH— group, with R as defined herein.

An "O-thiocarbamyl" group refers to a —OC(=S)—N(R)2, group with R as defined herein.

An "N-thiocarbamyl" group refers to an ROC(=S)NH— group, with R as defined herein.

A "C-amido" group refers to a —C(=O)—N(R)2 group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'— group, with R as defined herein, and R' being a diradical alkylene group. Examples of acylalkyl, without limitation, may include CH3C(=O)CH2-, CH3C(=O)CH2CH2-, CH3CH2C(=O)CH2CH2-, CH3C(=O)CH2CH2CH2-, and the like.

Unless otherwise indicated, when a substituent is deemed to be "optionally substituted," it is meant that the substituent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof.

The terms "protecting group" and "protecting groups" as used herein refer to any atom or group of atoms that is added to a molecule in order to prevent existing groups in the molecule from undergoing unwanted chemical reactions. The protecting group moiety may be chosen in such a way, that they are stable to the reaction conditions applied and readily removed at a convenient stage using methodology known from the art. A non-limiting list of protecting groups include benzyl; substituted benzyl; alkylcarbonyls (e.g., t-butoxycarbonyl (BOC)); arylalkylcarbonyls (e.g., benzyloxycarbonyl, benzoyl); substituted methyl ether (e.g. methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g. benzoate ester); carbonates (e.g. methoxymethylcarbonate); sulfonates (e.g. tosylate, mesylate); acyclic ketal (e.g. dimethyl acetal); cyclic ketals (e.g., 1,3-dioxane or 1,3-dioxolanes); acyclic acetal; cyclic acetal; acyclic hemiacetal; cyclic hemiacetal; and cyclic dithioketals (e.g., 1,3-dithiane or 1,3-dithiolane).

As used herein, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

As used herein, "heterocyclyl" means a cyclic ring system comprising at least one heteroatom in the ring system backbone. The heteroatoms are independently selected from oxygen, sulfur, and nitrogen. Heterocyclyls may include multiple fused rings. Heterocyclyls may have any degree of saturation provided that at least one ring in the ring system is not aromatic. Heterocyclyls may be substituted or unsubstituted, and are attached to other groups via any available valence, preferably any available carbon or nitrogen. Preferred monocyclic heterocycles are of 5 or 6 members. In six membered monocyclic heterocycles, the heteroatom(s) are selected from one up to three of oxygen, sulfur, and nitrogen, and wherein when the heterocycle is five membered, preferably it has one or two heteroatoms selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like. Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. The attachment point of a heterocycle radical can be at the position of a nitrogen heteroatom or via a carbon atom of the heterocycle.

The term "aryl" means a carbocyclic aromatic ring or ring system. Moreover, the term "aryl" includes fused ring systems wherein at least two aryl rings, or at least one aryl and at least one C3-8-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, C1-6 alkoxy, C1-6 alkyl, C1-6 hydroxyalkyl, C1-6 aminoalkyl, C1-6 alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-yl-phenyl, 4-pyrrolidin-1-ylphenyl, 4-pyrazolylphenyl, 4-triazolylphenyl, and 4-(2-oxopyrrolidin-1-yl)phenyl.

As used herein, the term "heteroaryl" means an aromatic radical having one or more heteroatom(s) (e.g., oxygen, sulfur, or nitrogen) in the ring backbone and may include a single ring (e.g., pyridine) or multiple condensed rings (e.g., quinoline). Heteroaryl groups can carry one or more substituents, each independently selected from halo, hydroxy, amino, cyano, nitro, cycloalkyl, haloalkyl, aryl, heterocyclyl, mercapto, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, and trifluoromethyl. Representative examples of heteroaryl groups include, but are not limited to, optionally substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents can be halo, hydroxy, cyano, O—$C_{1-6}$-alkyl, $C_{1-6}$-alkyl, hydroxy-$C_{1-6}$-alkyl, and amino-$C_{1-6}$-alkyl.

The term "platelet" is used here to refer to a blood platelet. A platelet can be described as a minisule protoplasmic disk occurring in vertebrate blood. Platelets play a role in blood clotting. The platelet may be derived from any source including a human blood supply, or the patient's own blood.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

Refrigerated storage is believed to reduce platelet lifespan due to decreased temperature that cause glycoprotein-Ib (GPIb) receptors to cluster on specific microdomains of the platelet membrane. Applicant has found that recognition of specific glycated/syalylated residues on clustered glycoproteins by macrophage β2 integrins and hepatocyte Ashwell-Morell receptors results in platelet phagocytosis by the host and removal from circulation. Thus, Applicant has identified prevention of glycoprotein clustering as a useful target for chemical intervention.

Platelet glycoproteins are intimately associated with intracellular cytoskeleton. Clustering of platelet glycoproteins depends on the formation of lipid raft in the platelet membrane, which in turn depends on the dynamics of the highly regulated processes of actomyosin assembly/disassembly. Rho family GTPases, including RhoA, Rac1 and Cdc42, are a class of GTP-binding enzymes that are central regulators of F-actin polymerization/depolymerization, and have been shown to control lipid raft formation and composition. Therefore, Applicant postulates that changes in Rho GTPase activities may influence platelet membrane lipid raft assembly and glycoprotein composition. Reversible targeting of Rho family GTPases by small molecule inhibitors may prevent cytoskeleton-dependent refrigeration storage lesions in platelets and result in increased platelet survival.

The mechanisms of how cold temperatures affect platelet survival are not completely understood, though significant information has been collected in the past decade. The effects of cold temperature on platelets are believed to be complex and involve shape change, cytoskeletal reorganization, activation, cell surface protein clustering and changes in the carbohydrate structures of surface glycoproteins (15-18). Refrigeration-induced changes including filopodia or lamellipodia are accompanied by an increase in the fraction of total cellular actin in a polymeric state (F-actin) (12, 18, 19) and disappearance of a peripheral microtubule coil (20). Isolated prevention of microtubule polymerization using colchicine has not resulted in shape change prevention upon activation (21, 22). Prevention of isolated actin dynamics using cytochalasin B results in reversion of discoid shape (18) but not in improved platelet survival in baboons (23), suggesting that irreversible blockade of actin polymerization does not prevent the refrigeration damage.

Presence of platelet cold receptors has been postulated as an explanation for both homeostatic and clinical effects when platelets are submitted to temperatures below 16° C. Cold temperature is believed to induce deglycosylation of glycoprotein Ib ectodomain exposing N-acetyl-D-glucosamine residues (17), which sequesters GM1 gangliosides in lipid rafts. Raft-associated glycoprotein Ibα forms clusters upon binding of 14-3-3z adaptor proteins to its cytoplasmic tail, a process accompanied with mitochondrial damage and PS exposure (apoptosis-like)(24). The mechanisms of platelet clearance are believed to be associated with lipid-raft associated GPIb clustering and prevention of clustering prevents platelet clearance (15, 25). Intimately associated with intracellular cytoskeleton, GPIb clustering depends on the formation of microdomains (so-called "lipid rafts") in the platelet membrane which in turn depends on the dynamics of the highly regulated processes of acto-myosin assembly/disassembly at multiple levels. In summary, refrigeration results in multiple, complex platelet defects that may be closely associated with cytoskeletal impairments at multiple levels (FIG. IA).

Figure 1B:
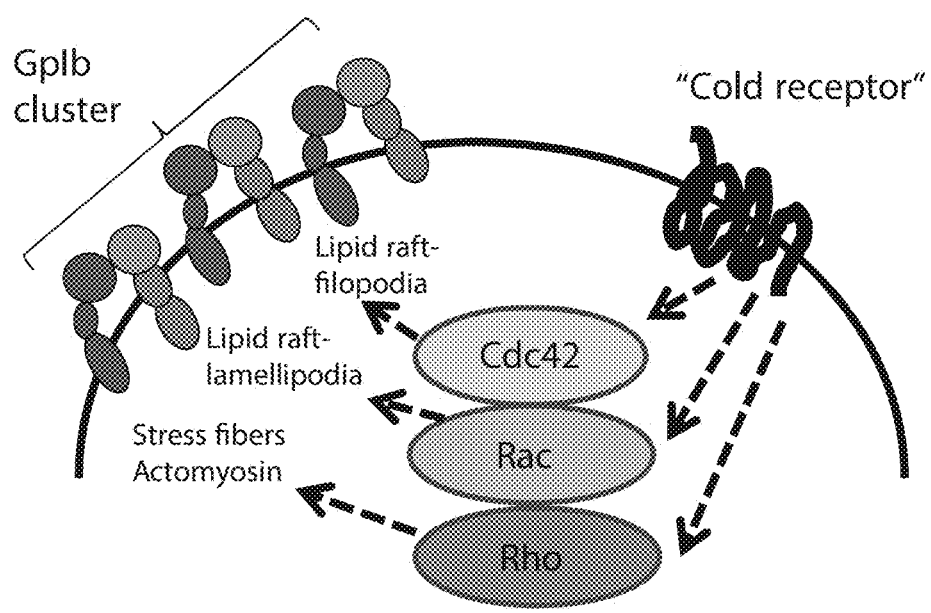

Actin cytoskeletal rearrangements responsible for lipid rafts and GPIb clustering in lipid rafts depends on the coordinated activities of Cdc42, Rac1 and RhoA GTPases, which control specific downstream effectors in regulating polymerization and depoymerization of F-actin, actomyosin contraction, tubulin polymerization, and spectrin anchorage. The Rho family GTPases are a class of GTP-binding enzymes that act as signaling switches in spatial/temporal transduction and amplification of signals from platelet receptors to the intracellular signaling pathways that drive platelet function. Among the direct Rho GTPase effectors, WASPs, formins and PAKs that control F-actin polymerization/depolymerization have been shown to be crucial in the control of lipid raft formation and composition and tubular polymerization of platelets (27) (FIG. 1B). Therefore, changes in Rho GTPase activities may influence platelet membrane microdomain assembly and glycoprotein composition. Earlier studies using dominant negative mutants of Cdc42 and Rac1 found no effect on prevention of cold-induced platelet damage (28), but the limitation of the tools used has prevented investigators from manipulating actin/actomyosin dynamics in a specific, reversible fashion.

Without intending to be limited by theory, it is believed that reversible inhibition of multiple Rho family of GTPases by chemical inhibitors can significantly improve platelet survival and transfusion function after refrigerated storage by interference with actomyosin dynamics and membrane microdomains to prevent GPIb clustering.

Compositions and methods useful for platelet survival and/or quality, transfusion, and associated issues are disclosed herein. In one aspect, a composition for platelet storage or treatment is described. The composition may comprise a RAC inhibitor, for example, those described in U.S. Pat. Nos. 7,517,890 and 7,612,080, a CDC42 inhibitor, for example, those described in U.S. Pat. No. 8,383,124; a RHOA inhibitor, and combinations thereof.

In one aspect, the RAC inhibitor may comprise a compound having the structure of Formula I or a pharmaceutically acceptable salt thereof:

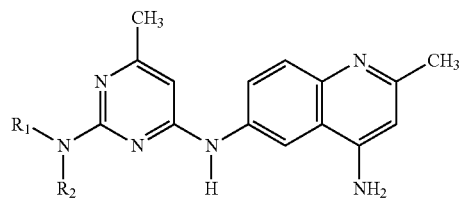
(Formula I)

wherein
$R_1$ to $R_2$ are independently selected from the group consisting of H, —X-Alk, —X-Alk-X', and —X—Y—X'; wherein
X is —$CR_7R_8$;
X' is —$CHR_7R_8$;
Alk is a $C_2$-$C_{18}$ substituted or unsubstituted hydrocarbon chain;
Y is a $C_2$-$C_8$ substituted or unsubstituted alkylene chain;
$R_6$ is H or ($C_1$-$C_4$) alkyl; and
$R_7$ and $R_8$ are independently selected from the group consisting of H and ($C_1$-$C_4$) alkyl;
or a salt thereof;

In one aspect, the RAC inhibitor may comprise the structure of Formula Ia or a pharmaceutically acceptable salt thereof.

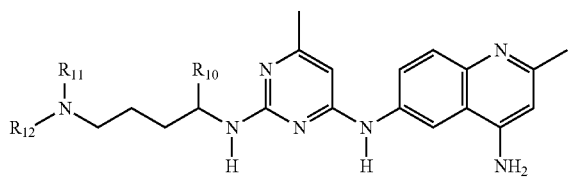
(Formula Ia)

wherein:
$R_{10}$ to $R_{12}$ are independently selected from the group consisting of H, halo, ($C_1$-$C_4$) alkyl, branched ($C_3$-$C_4$) alkyl, halo ($C_1$-$C_4$) alkyl, ($C_1$-$C_4$) alkoxy, $NO_2$, and $NH_2$.

In one aspect, the RAC inhibitor may comprise Formula Ib or a pharmaceutically acceptable salt thereof.

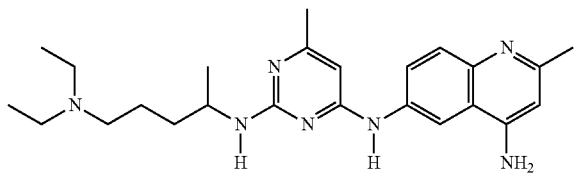
(Formula Ib)

In one aspect, the CDC42 inhibitor may comprise Formula II or a pharmaceutically acceptable salt thereof.

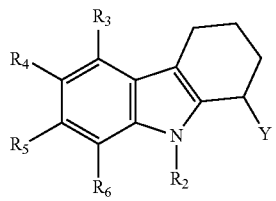
(Formula II)

wherein
Y is selected from the group consisting of $OR_7$, $NR_8R_9$, and $NNR_8R_9$;
$R_7$ is selected from the group consisting of $C_{1-6}$ alkyl, $(CH_2)uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH2)uC_{3-7}$ cycloalkyl, $C_{2-6}$ alkenyl, $C_{1-6}$ alkoxy, hydroxy-$C_{1-6}$ alkyl, phenyl are each optionally substituted with one or more substituents each independently selected from the group consisting of halo, —CN, —OH, $C_{1-6}$ alkoxyl, heteroaryl, $R_{19}$, and $OR_{20}$;
$R_8$ and $R_9$ may each be separately a hydrogen, or separately selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)$ $uC_{3-7}$cycloalkyl, $C_{2-6}$ alkenyl, $C_{1-6}$ alkoxy, hydroxy-$C_{1-6}$ alkyl, $R_{19}$, $OR_{20}$, $C_{1-6}$ alkyl substituted with up to 5 fluoro, and $C_{1-6}$ alkoxy substituted with up to 5 fluoro, each optionally substituted with one or more substituents each independently selected from the group consisting of halo, cyano, nitro, hydroxy, $C_{1-6}$ alkyl, and $C_{1-6}$ alkoxy; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, $(CH_2)uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;
each u is independently 0, 1, 2, 3, or 4;
$R_2$ is a hydrogen, or selected from the group consisting of $C_{1-6}$ alkyl, $C_{3-7}$cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and —$O(CH_2)$uphenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_5$ and $R_6$ are each independently selected from the group consisting of: hydrogen, halo, cyano, nitro, hydroxy, $C_{1-6}$ alkyl, $(CH_2)uC_{3-7}$cycloalkyl, —$O(CH_2)uC_{3-7}$ cycloalkyl, $C_{2-6}$ alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)uC_{3-7}$cycloalkyl, —$O(CH2)uC_{3-7}$cycloalkyl, $C_{2-6}$ alkenyl, $C_{1-6}$ alkoxy, hydroxy-$C_{1-6}$ alkyl, and phenyl, each optionally substituted with one or more substituents each independently selected from the group consisting of halo, cyano, nitro, hydroxy, $C_{1-6}$ alkyl, —$(CH_2)uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, —$(CH_2)uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

$R_{19}$ is aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

$R_{20}$ is hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$, is not substituted with hydroxyl.

In one aspect, the CDC42 inhibitor may comprise Formula II, or a pharmaceutically acceptable salt thereof

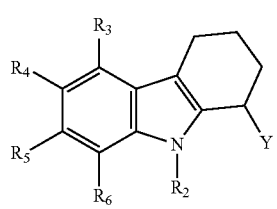

(Formula II)

wherein:
Y is $NR_8R_9$,
$R_8$ is hydrogen; and $R_9$ is $C_{1-6}$ alkyl, said $C_{1-6}$ alkyl, optionally substituted with one or more substituents each independently selected from the group consisting of hydroxy, $R_{19}$ or $OR_{20}$;

$R_{19}$ is phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and $R_{20}$ is hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In one aspect, the CDC42 inhibitor may comprise Formula IIa (CASIN), or a pharmaceutically acceptable salt thereof

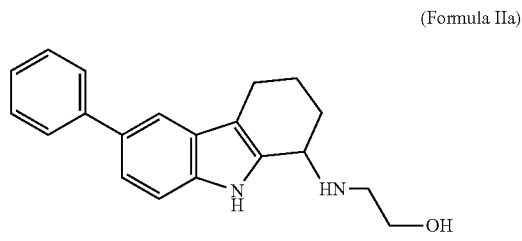 [SMILES: OCCNC1CCCc2c1[nH]c1ccc(-c3ccccc3)cc21]

(Formula IIa)

In one aspect, the RHOA inhibitor may comprise (Formula III)(G04), or a pharmaceutically acceptable salt thereof.

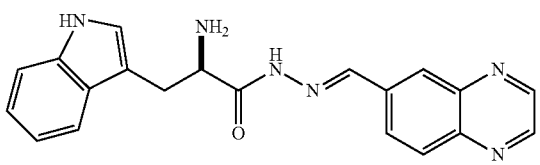

(Formula III)

(G04)

In one aspect, the composition may comprise the Formula 1b (NSC23766) or a pharmaceutically acceptable salt thereof, Formula IIa (CASIN) or a pharmaceutically acceptable salt thereof; Formula III (G04) or a pharmaceutically acceptable salt thereof, and combinations thereof.

Any amine, hydroxy, or carboxyl side chain on the compounds of the may be esterified or amidified. The procedures and specific groups to be used to achieve this end are known to those of skill in the art.

Synthesis of one or more of the above-referenced compounds may be describes in, for example, U.S. Pat. No. 8,383,124 to Zheng, issued Feb. 26, 2013; U.S. Pat. No. 7,612,080 to Zheng et al., issued Nov. 3, 2009; and U.S. Pat. No. 7,517,890 to Zheng et al, issued Apr. 14, 2009, the contents of which are incorporated by reference for all purposes.

The active agent can form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts")

can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

The active agents which contain a basic moiety, such as, but not limited to an amine or a pyridine or imidazole ring, can form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The active agents that contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Active agent, and salts thereof, can exist in their tautomeric form (for example, as an amide or imino ether). All such tautomeric forms are contemplated herein as part of the preferred embodiments.

All stereoisomers of the present compounds, such as those, for example, which can exist due to asymmetric carbons on any of the substituents, including enantiomeric forms (which can exist even in the absence of asymmetric carbons) and diastereomeric forms, are contemplated and within the scope of the preferred embodiments. Individual stereoisomers of the compounds of the preferred embodiments can, for example, be substantially free of other isomers, or can be admixed, for example, as racemates or with all other or other selected, stereoisomers. The chiral centers of the preferred embodiments can have the S or R configuration as defined by the IUPAC 1974 Recommendations.

When the compounds are in the forms of salts, they may comprise pharmaceutically acceptable salts. Such salts may include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts may be prepared by methods known to one of ordinary skill in the art. For example, by reacting the active agent with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents can be used. Organic bases like lysine, arginine, diethanolamine, choline, guandine and their derivatives etc. can also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents can also be used.

In one aspect, any of the above-described compositions may comprise a physiologically acceptable carrier. In one aspect, the physiologically acceptable carrier may comprise a buffer. In one aspect, the physiologically acceptable carrier may be selected from saline, phosphate buffered saline, Tris buffered saline, Hank's buffered saline, water, or a combination thereof. In one aspect, the physiologically acceptable carrier may comprise an electrolyte solution.

In one aspect, the RAC inhibitor, the CDC42 inhibitor, and the RHOA inhibitor may be present in a carrier at a concentration, in combination or separately, of at least about 10 μM, or at least about 25 μM, at least about 50 μM, at least about 100 lM, at least about 200 μM, at least about 500 μM, at least about 1 mM, at least about 10 mM, at least about 50 mM, at least about 100 mM, or at least about 1 M.

In one aspect, the RAC inhibitor may be present at a concentration of from about 10 μM to about 500 μM, or from about 25 μM to about 400 μM, or from about 50 μM to about 300 μM, or from about 75 μM to about 200 μM, or from about 100 μM to about 150 μM, or about 50 μM.

In one aspect, the CDC42 inhibitor may be present at a concentration of from about 5 µM to about 500 µM, or from about 10 µM to about 400 µM, or from about 25 µM to about 300 µM, or from about 50 µM to about 200 µM, or from about 75 µM to about 150 µM, or about 10 µM.

In one aspect the RHOA inhibitor may be present at a concentration of from about 10 µM to about 500 µM, or from about 25 µM to about 400 µM, or from about 50 µM to about 300 µM, or from about 75 µM to about 200 µM, or from about 100 µM to about 150 µM, or about 75 µM.

In further aspects, the described compositions may comprise an additive selected from NaCl, KCl, CaCl2, MgCl$_2$, MgSO$_4$, Na$^3$ citrate, citric acid, NaHCO$_3$, Na phosphate, Na acetate, Na gluconate, glucose, maltose, mannitol, and combinations thereof. The described compositions may comprise an additive selected from NaCl, KCl, CaCh, MgCl$_2$, MgSO$_4$, Na$^3$ citrate, citric acid, NaHCO$_3$, Na phosphate, Na acetate, Na gluconate, glucose, maltose, mannitol, and combinations thereof, wherein said additive may be present in an amount of from about 0.5 mmol/L to about 150 mmol/L.

In further aspects, the described compositions may comprise one or more ingredients selected from D-ribose, D-glucose, Hanks solution, Hepes solution, bovine serum albumin, tic anticoagulant peptide and sterile water, or combinations thereof.

In one aspect, the composition may comprise an auxiliary substance selected from pH adjusting and buffering agents, tonicity adjusting agents, stabilizers, wetting agents, and combinations thereof.

In one aspect, the composition may have a pH of from about 5 to about 8, or from about 6 to about 7, or about 6.8 to about 7.4.

In one aspect, the composition may be isotonic.

In yet further aspects, the composition may comprise an additional therapeutic agent.

A method for storing platelets is also described. In this aspect, the method comprises the step of storing platelets in a composition as disclosed herein.

In one aspect, the method may comprise contacting platelets with a solution comprising an RAC inhibitor, an CDC42 inhibitor, and/or a RHOA inhibitor, wherein the one or more actives are present in a carrier at a concentration, in combination or separately, of at least about 10 µM, or at least about 25 µM, at least about 50 µM, at least about 100 µM, at least about 200 µM, at least about 500 µM, at least about 1 mM, at least about 10 mM, at least about 50 mM, at least about 100 mM, or at least about 1 M.

In one aspect, the method may comprise contacting platelets with a solution comprising an RAC inhibitor present in a solution at a concentration of from about 10 µM to about 500 µM, or from about 25 µM to about 400 µM, or from about 50 µM to about 300 µM, or from about 75 µM to about 200 µM, or from about 100 µM to about 150 µM, or about 50 µM.

In one aspect, the method may comprise contacting platelets with a solution comprising a CDC42 inhibitor present in a solution at a concentration of from about 5 µM to about 500 µM, or from about 10 µM to about 400 µM, or from about 25 µM to about 300 µM, or from about 50 µM to about 200 µM, or from about 75 µM to about 150 µM, or about 10 µM.

In one aspect, the method may comprise contacting platelets with a solution comprising an RHOA inhibitor present in a solution at a concentration of from about 10 µM to about 500 µM, or from about 25 µM to about 400 µM, or from about 50 µM to about 300 µM, or from about 75 µM to about 200 µM, or from about 100 µM to about 150 µM, or about 75 µM.

In one aspect, the storage step may be carried out at a temperature of from about 1° C. to about 20° C., or at about 1° C., or about 2° C., or about 3° C., or about 4° C., or about 5° C., or about 6° C., or about 7° C., or about 8° C., or about 9° C., or about 10° C., or about 11° C., or about 12° C., or about 13° C., or about 14° C., or about 15° C., or about 16° C.

In one aspect, the storage step may be carried out for a period of time of from about 7 to 20 days, or from about 10 to 15 days, or greater than 7 days, or greater than 8 days, or greater than 9 days, or greater than 10 days, or greater than 11 days, or greater than 12 days, or greater than 13 days, or greater than two weeks.

In one aspect, the composition may be used in an amount sufficient to inhibit a platelet damaging activity selected from polymerization of F-actin, depolymerization of F-actin, actomyosin contraction, tubulin polymerization, spectrin anchorage, or combinations thereof.

In one aspect, applying the described methods, the platelet survival may be greater than about 65%, or greater than about 70%, or greater than about 75%, or greater than about 80%, or greater than about 85%, or greater than about 90%, or greater than about 95%, or greater than about 99% after a storage period of 24 hours at 5 C.

In one aspect, a method of reversing platelet activation is also disclosed, comprising contacting activated platelets with a composition as described herein. In one aspect, the contacting step may be carried out at a temperature of about 0° C. In a yet further aspect, the disclosed compositions may be used to reverse refrigeration storage lesions in platelets. In this aspect, platelets having refrigeration storage lesions may be contacted with a composition as disclosed herein, for a period of time sufficient to reverse refrigeration storage lesions.

EXAMPLES

Figure 2:
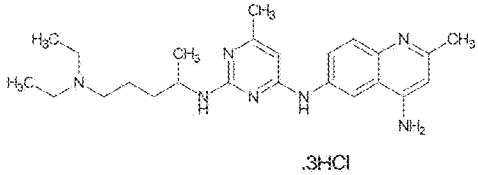
FIG. 2 depicts Rho GTPases inhibitor chemical structures and targets.
Figure 2:
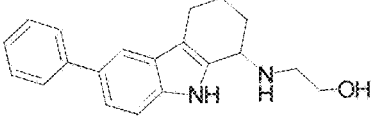
Figure 2:
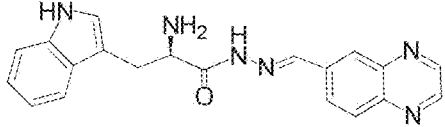
Figure 3A:
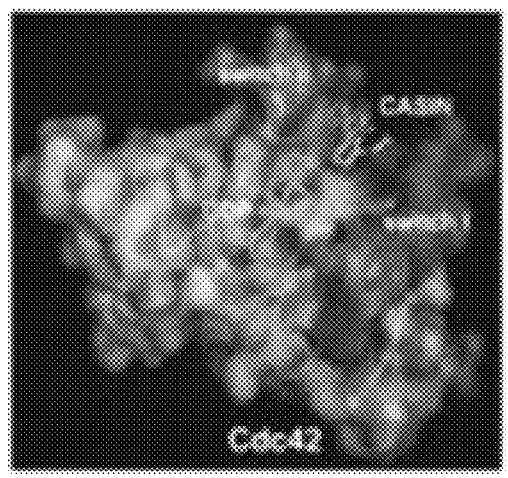
FIGS. 3A-3D depict a docking model of Casin bound to Cdc42 surface groove and data demonstrating Casin activity.
Figure 3B:
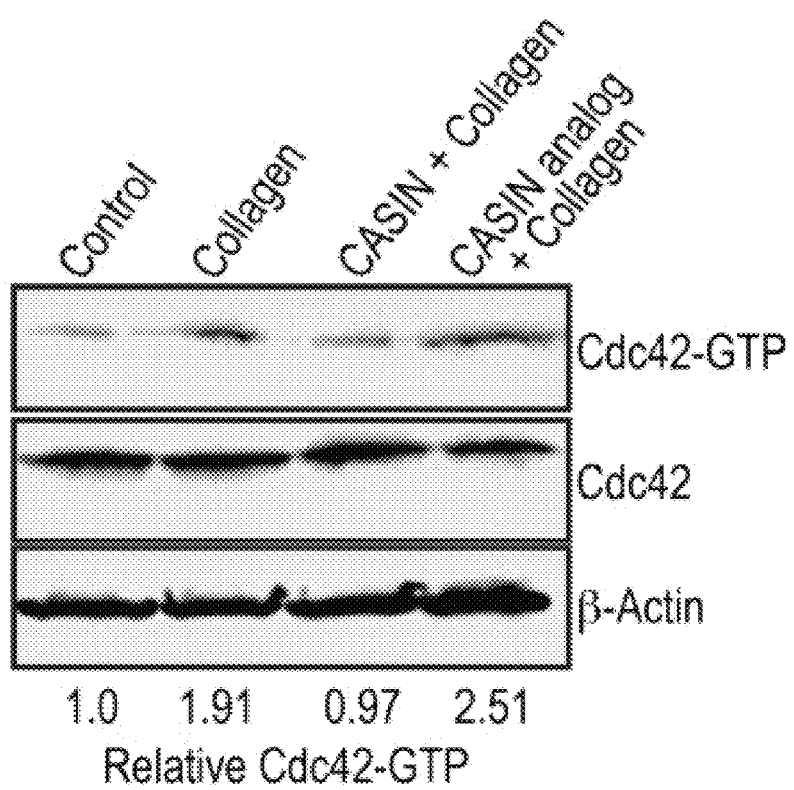
Figure 3C:
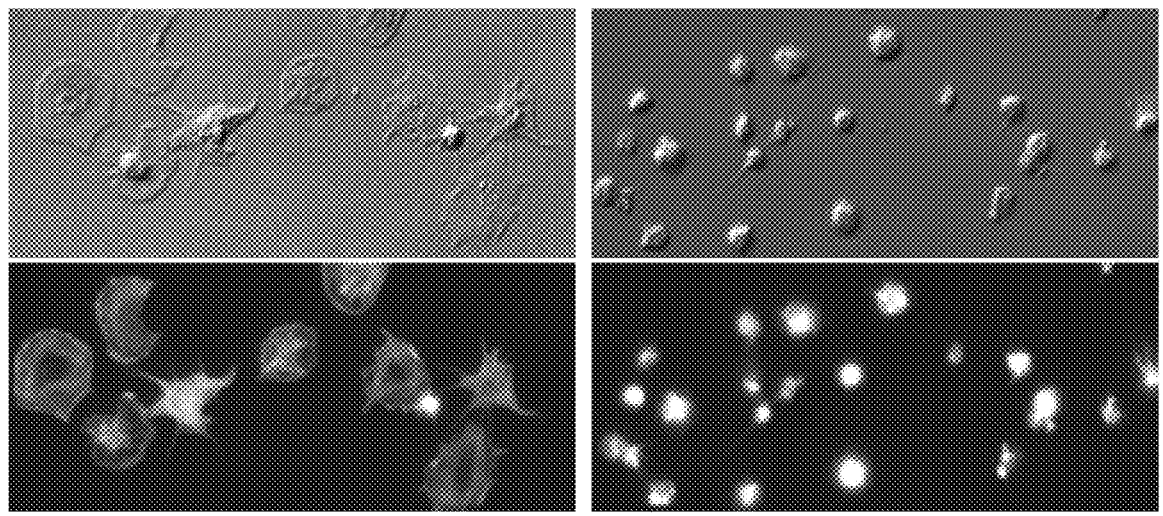
Figure 3D:
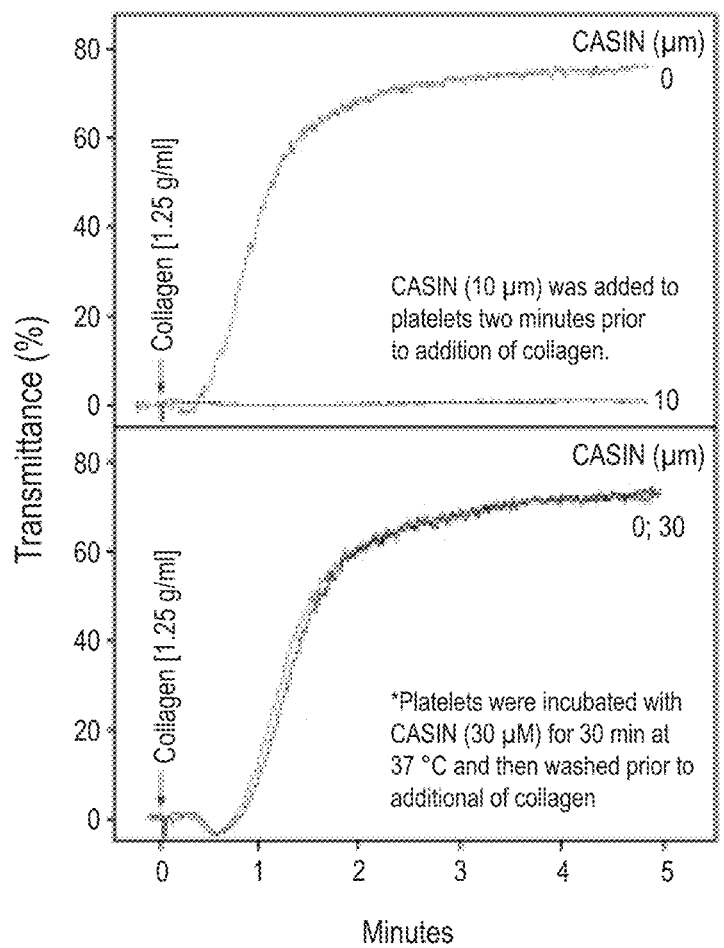

Applicant has tested the ability of three chemical inhibitors, CASIN, NSC23766 and G04, targeting Cdc42, Rac1 and RhoA, respectively (FIG. 2), to inhibit the activity of the GTPases and the consequent cytoskeleton-dependent functions of human platelets. A rationally developed inhibitor of Cdc42 with activity on activation by guanine nucleotide exchange factors is CASIN (29, *Nature Biotech* under revision). CASIN was recently discovered by Zheng group as a small molecule that recognizes a pocket domain that specifically blocks the ability of GEF interaction with Cdc42 (FIG. 3A). CASIN is found to suppress of hematopoietic stem cell aging through its specific Cdc42 inhibitory activity (29). In platelets, it inhibits Cdc42 activation (FIG. 3B) and prevents collagen-induced platelet shape changes (FIG. 3C). These changes depend on integrin signaling and involve F-actin polymerization and filopodia formation as demonstrated by phalloiding staining (FIG. 3C, lower panels). Cdc42 inhibition by CASIN results in prevention of collagen-induced platelet aggregation (FIG. 3D) that can be reversed by a washout of the inhibitor (FIG. 3D, upper and lower panels).

Figure 4A:
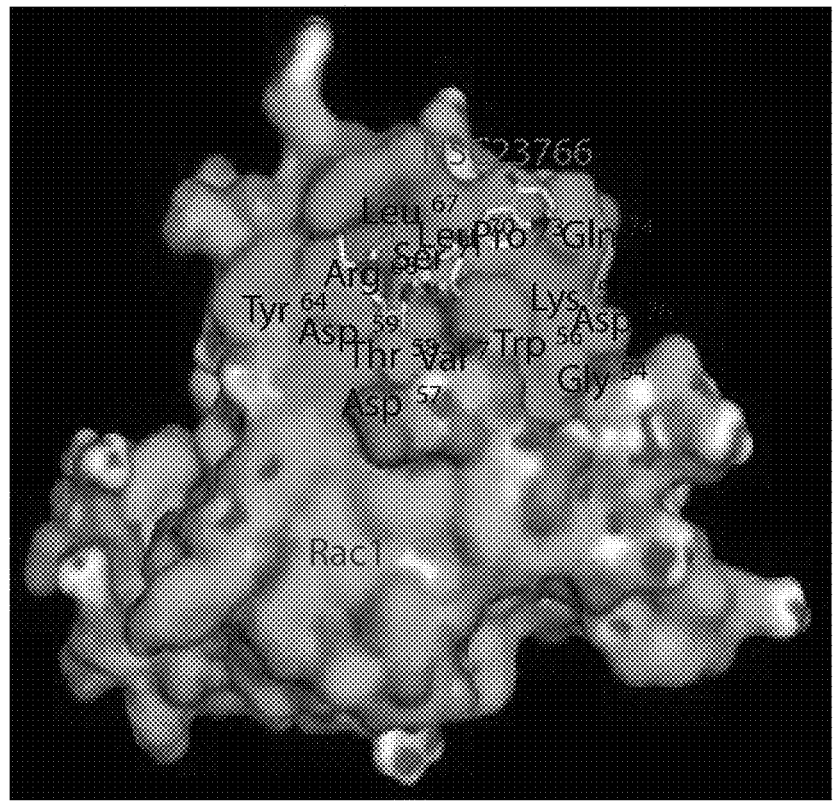
FIGS. 4A-4E depict a docking model of Rac inhibitor NSC23766 and data showing NSC23766 activity.
Figure 4B:
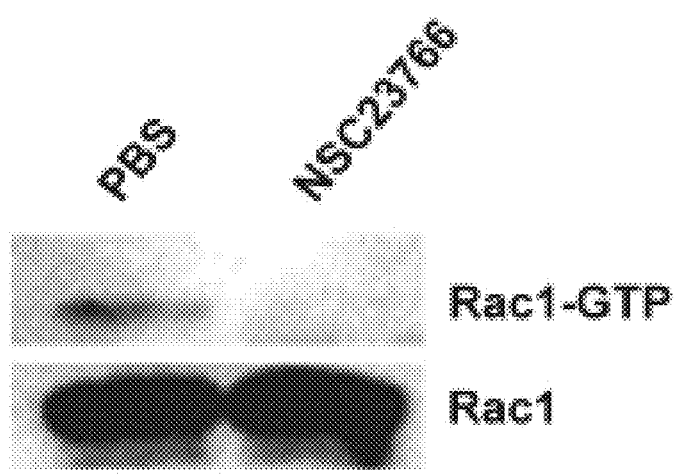
Figure 4C:
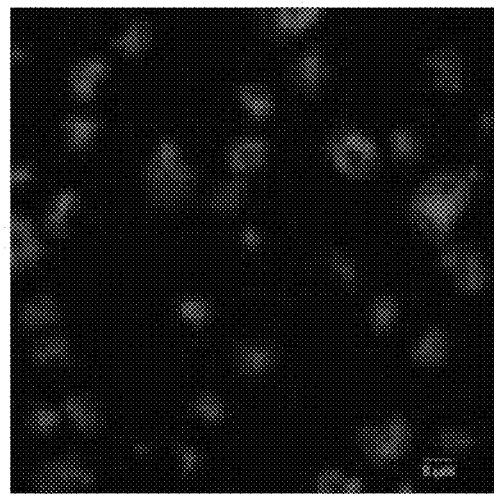
Figure 4C:
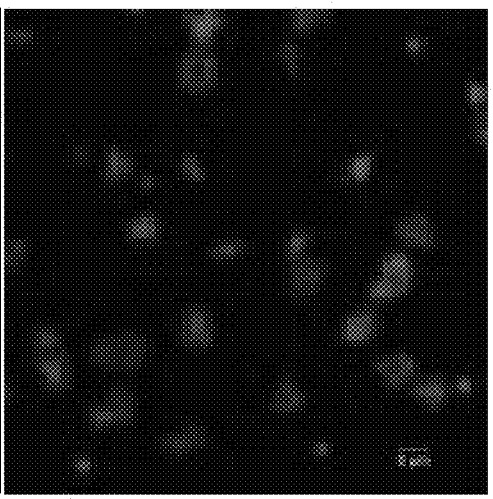
Figure 4D:
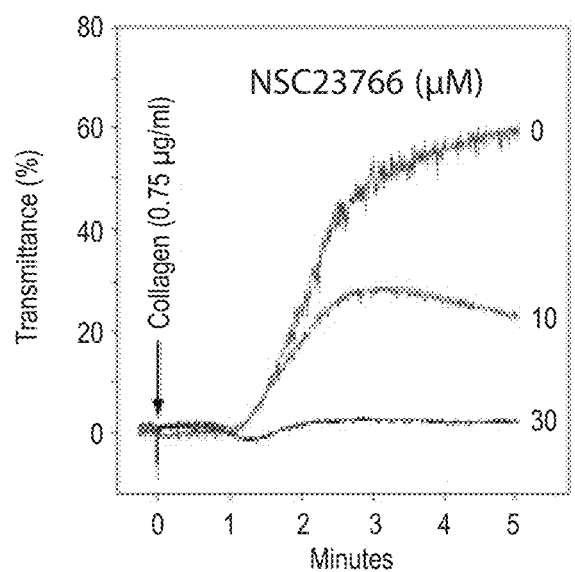
Figure 4E:
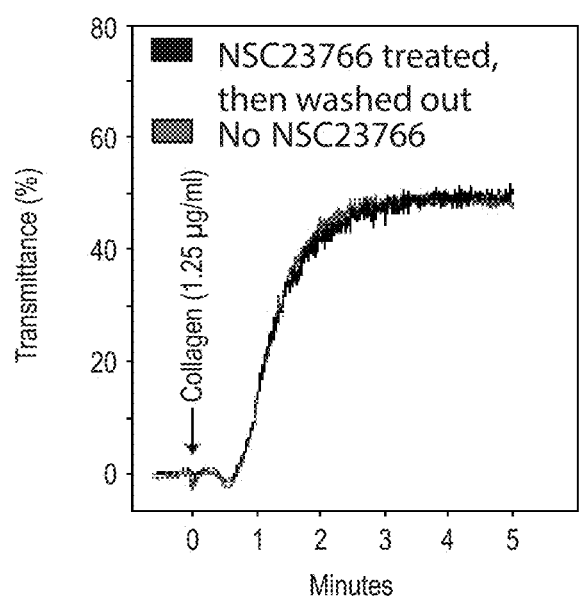

Similarly, Applicant has identified an inhibitor of Rac, NSC23766 (30-34), with an ability to impair Rac1 activation by multiple activating signals which may be crucial in platelet signaling associated with GpIb/GpX (35). NSC23766 was discovered in a structure-based virtual screening of compounds that fit into a surface groove of Rac 1 known to be critical for guanine nucleotide exchange factor specification (34) (FIG. 4A). NSC23766 can effectively block Rac1 activation (FIG. 4B) and Rac-dependent cytoskeletal rearrangements (actin lamellopodia) of platelets stimulated by collagen (30, 32, 35), indicating its ability for suppressing collagen-integrin dependent signaling (FIG. 4C). Finally, NSC23766 reversibly inhibits, in a dose-dependent fashion, platelet aggregation induced by collagen (FIG. 4D, upper and lower panels).

Figure 5A:
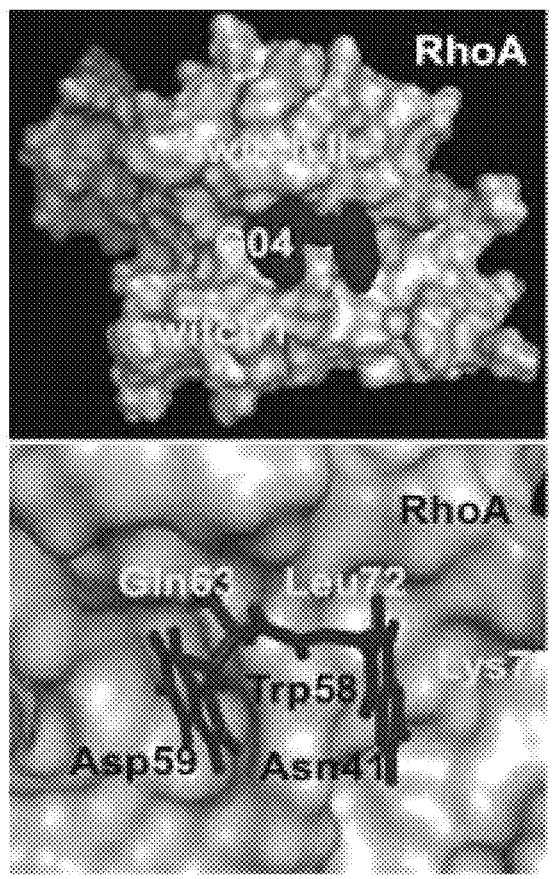
FIGS. 5A-5D depict a docking model of Rho inhibitor G04 and data showing G04 activity.
Figure 5B:
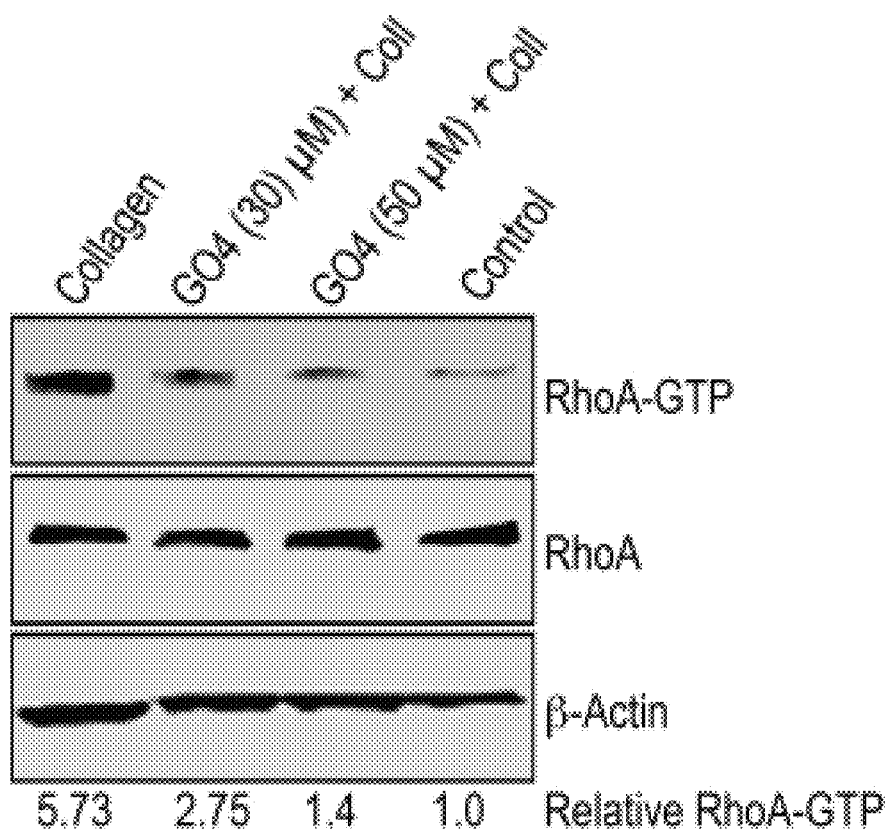
Figure 5C:
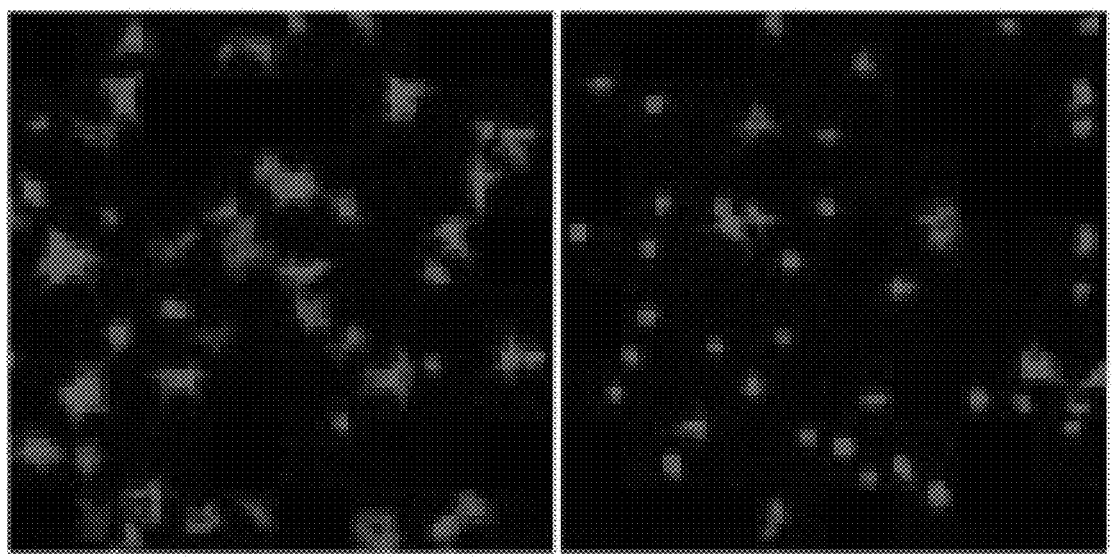
Figure 5D:
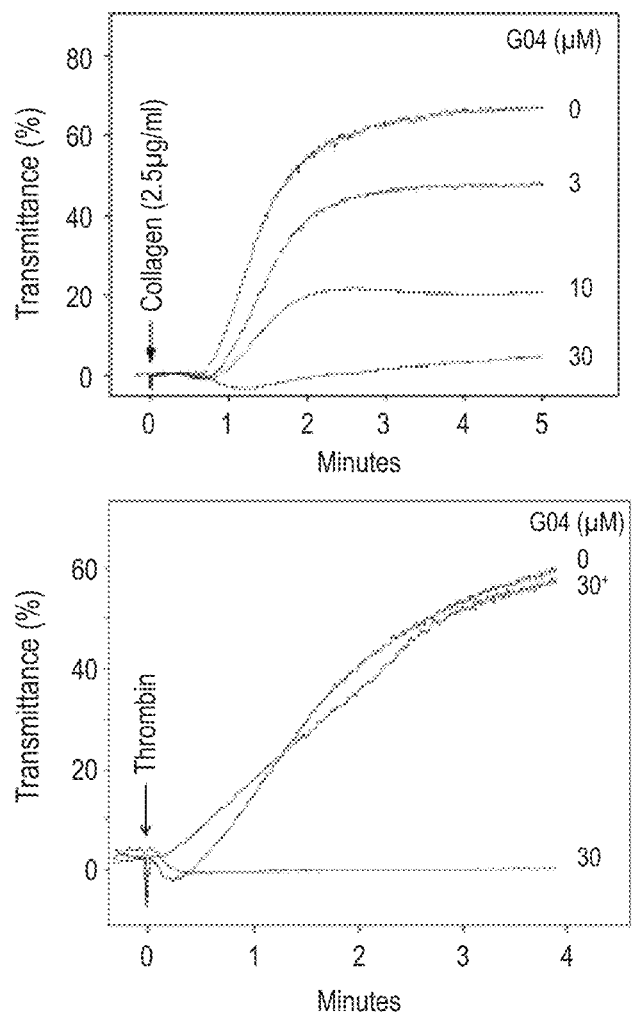

Finally, G04/Rhosin was also developed by us as a RhoA GTPase activation site inhibitor that transiently and specifically blocks RhoA activity and RhoA-mediated signaling functions (36, 37). G04 contains two aromatic rings tethered by a linker, and it binds to the surface area sandwiching Trp58 of RhoA (FIG. 5A) with a submicromolar Kd and effectively inhibits GEF-catalyzed RhoA activation. In platelets, G04 specifically inhibits collagen-induced RhoA activity (FIG. 5B) and RhoA-mediated cellular functions including fibrinogen-dependent platelet spreading (FIG. 5C) and collagen-dependent platelet aggregation (FIG. 5D). Effect by collagen or thrombin is reversible (FIG. 5D, lower).

In addition to the reversibility, each inhibitor transiently mimics the effects of Cdc42, Rac1, or RhoA gene knockout in platelets, respectively, and does not show any additive effects in the respective knockout cells (data not shown), indicating their specificity and a lack of toxicity.

Figure 6A:
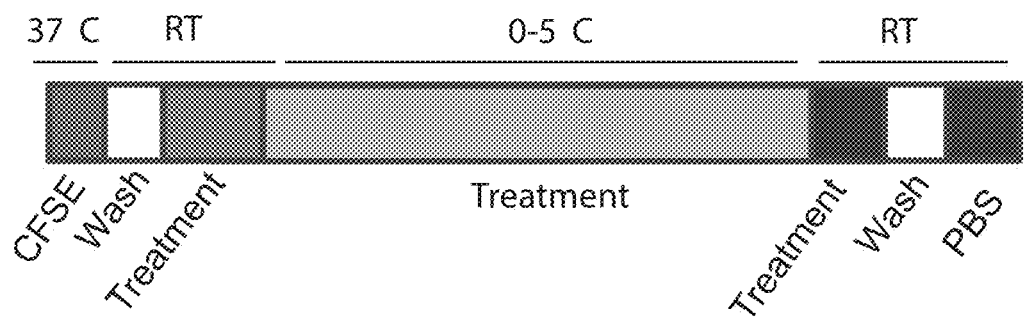
FIGS. 6A-6D depict the effects of Rho GTPase inhibitor treatment on platelet transfusion.
Figure 7:
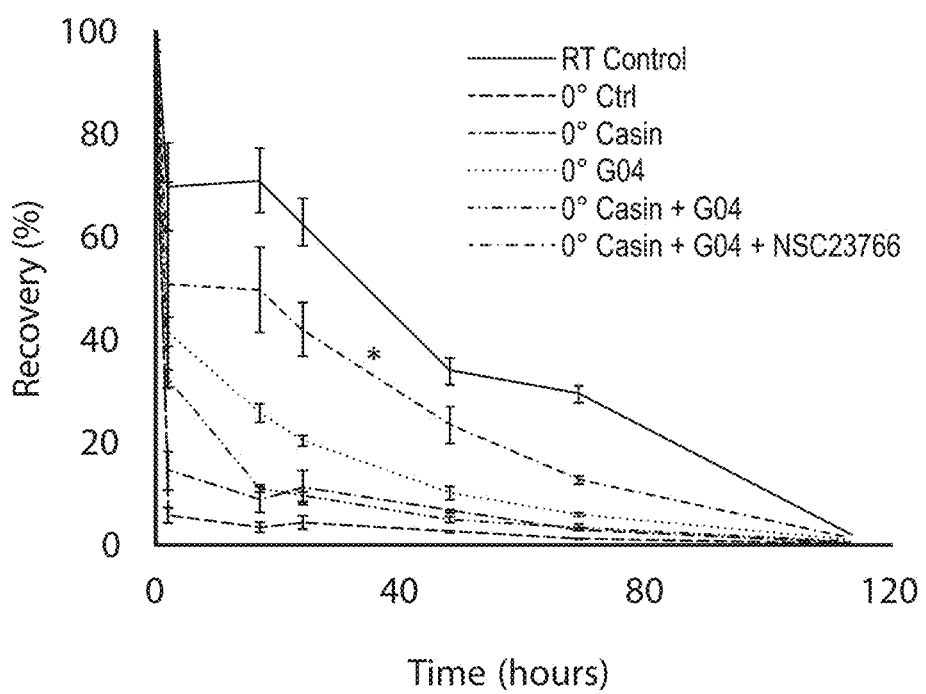
FIG. 7 depicts effects of Rho GTPase inhibitor combinations on platelet survival upon transfusion. Platelet recovery at different time points is shown. Donor platelets were stored at room temp (squares) or pretreated with a mixed Rho GPase inhibitors (50 uM NSC23766, 10 uM CASIN and/or 75 uM G04) or no drug (Ctrl). Data are presented as mean±SD. *p<0.01 (Anova test with Bonferroni correction, between refrigerated with no inhibitor and refrigerated with triple inhibitor combination).

A combination of CASIN (10 µM), G04 (75 µM) and/or NSC23766 were used in C57Bl/6 murine carboxyfluorescein-labeled platelets incubated at 0° C. or 5° C. for 3.5 hours. After re-warming, platelets were infused in 5 congenic mice (per group) and compared with control (room temperature stored) and refrigerated, untreated platelet group (FIG. 7). While the combination of NSC23766, G04 and CASIN result in close-to-complete reversal of the survival deficiency induced by refrigerated storage, NSC23766 alone or NSC23766 in combination with CASIN or G04 did not result in significant reversal of the storage lesion of platelets (FIG. 7). In a second experiment focused on the specific combinations with more activity to reverse the survival impairment associated with the use of Rho GTPase inhibitors, we analyzed the 24-hour recovery (%) and survival (hours) of platelets that had been stored in presence of several combinations of drugs (FIG. 6A).

Figure 6B:
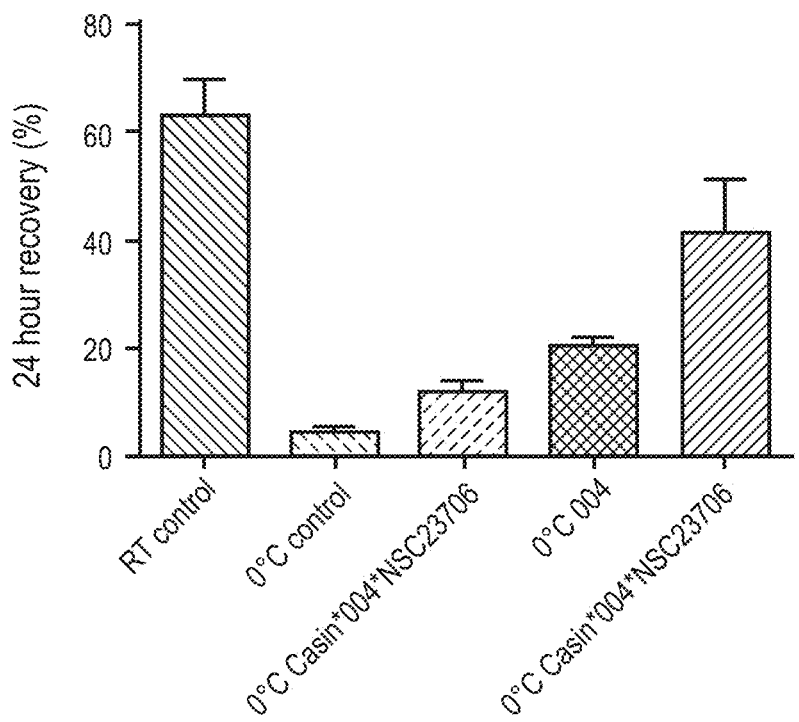
Figure 6C:
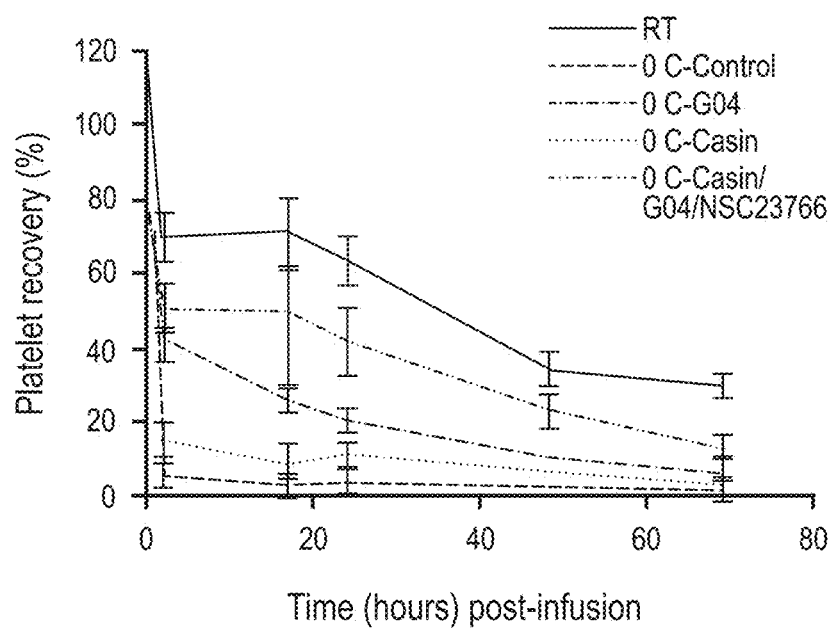
Figure 6D:
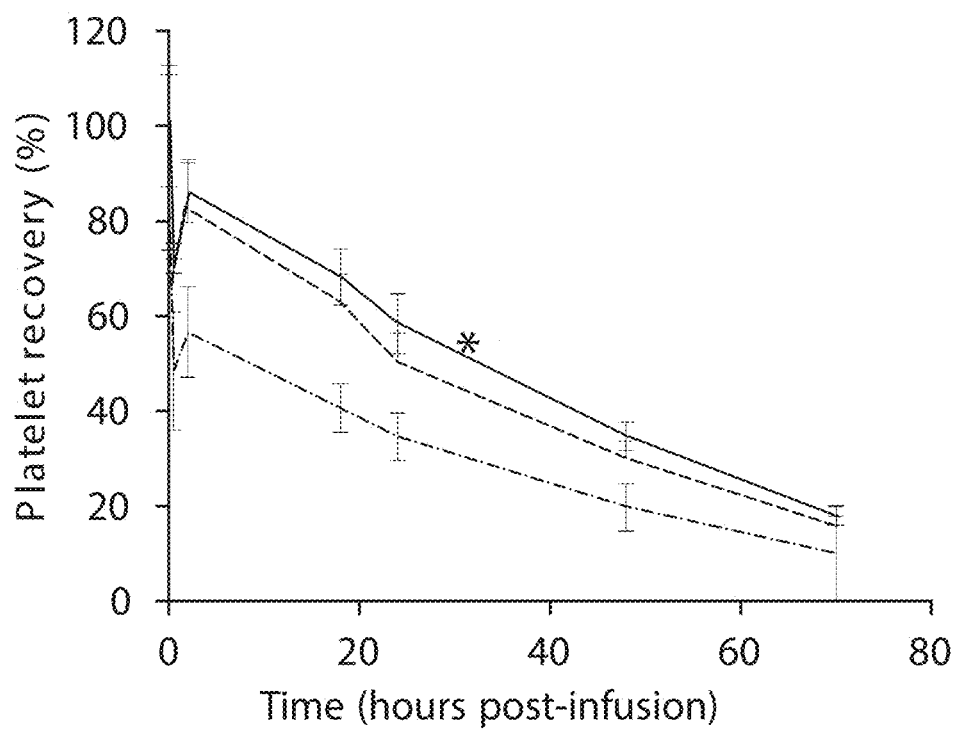

Similarly, treatment of refrigerated platelets with CASIN or G04 alone did not improve platelet 24-hour recovery (FIG. 6B) or survival (FIG. 6C) in vivo. However, a triple combination of CASIN, G04 and NSC23766 resulted in a significant improved recovery (FIG. 6B) and survival (FIG. 6C) of refrigerated platelets after infusion. Use of the same triple inhibitor combination during storage of refrigerated platelets at 5° C. instead of 0° C. resulted in complete reversal of the recovery and survival of refrigerated platelets in vivo (FIG. 6D) as determined by multi-hit regression analysis (COSTCO software) and ANOVA test with Bonferroni correction for statistical differences. Applicant found that the 24-hour recovery of platelets refrigerated was significantly reduced (~20%) compared with the group control (stored at room temperature, $p<0.01$). Interestingly, the shortened recovery was completely reversed by incubation with the cocktail of three inhibitors (FIG. 6D). Altogether, these data indicate that the inhibitory combination of Cdc42, Rac1, and RhoA with CASIN, NSC23766 and G04 can specifically and reversibly inhibit platelet activation and may be useful in a reversal of refrigeration storage lesion in platelets.

Figure 8:
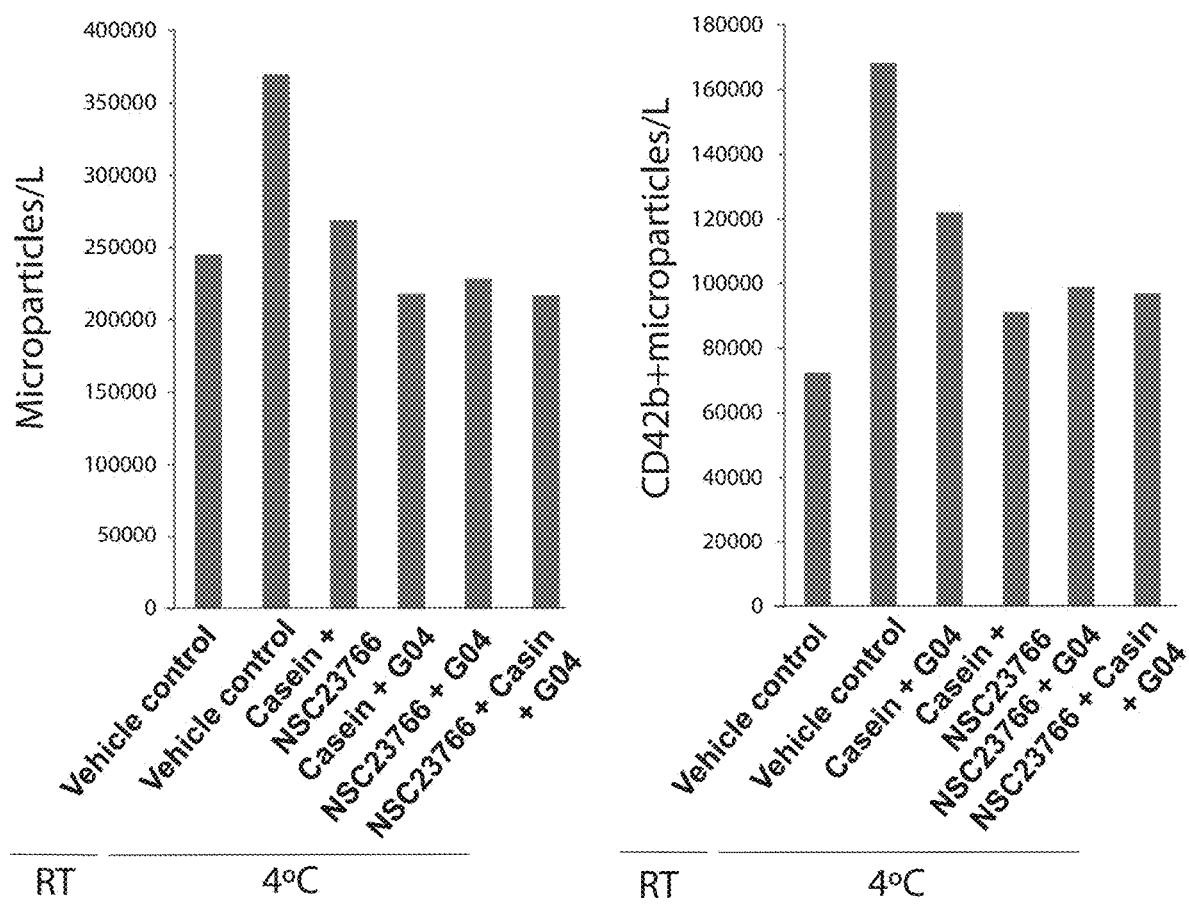
FIG. 8 depicts total microparticle and G plb+ microparticle counts from platelets stored in different conditions. Results are representative of three independent experiments with similar results of platelets stored for 6 days in 50 μM NSC23766, 10 μM CASIN and/or 75 μM G04, or no drug (Vehicle control). The left panel shows microparticles/mcL of refrigerated stored platelets for 6 days; the right panel shows Gplb+ microparticle counts of refrigerated stored platelets for 6 days.
Figure 9:
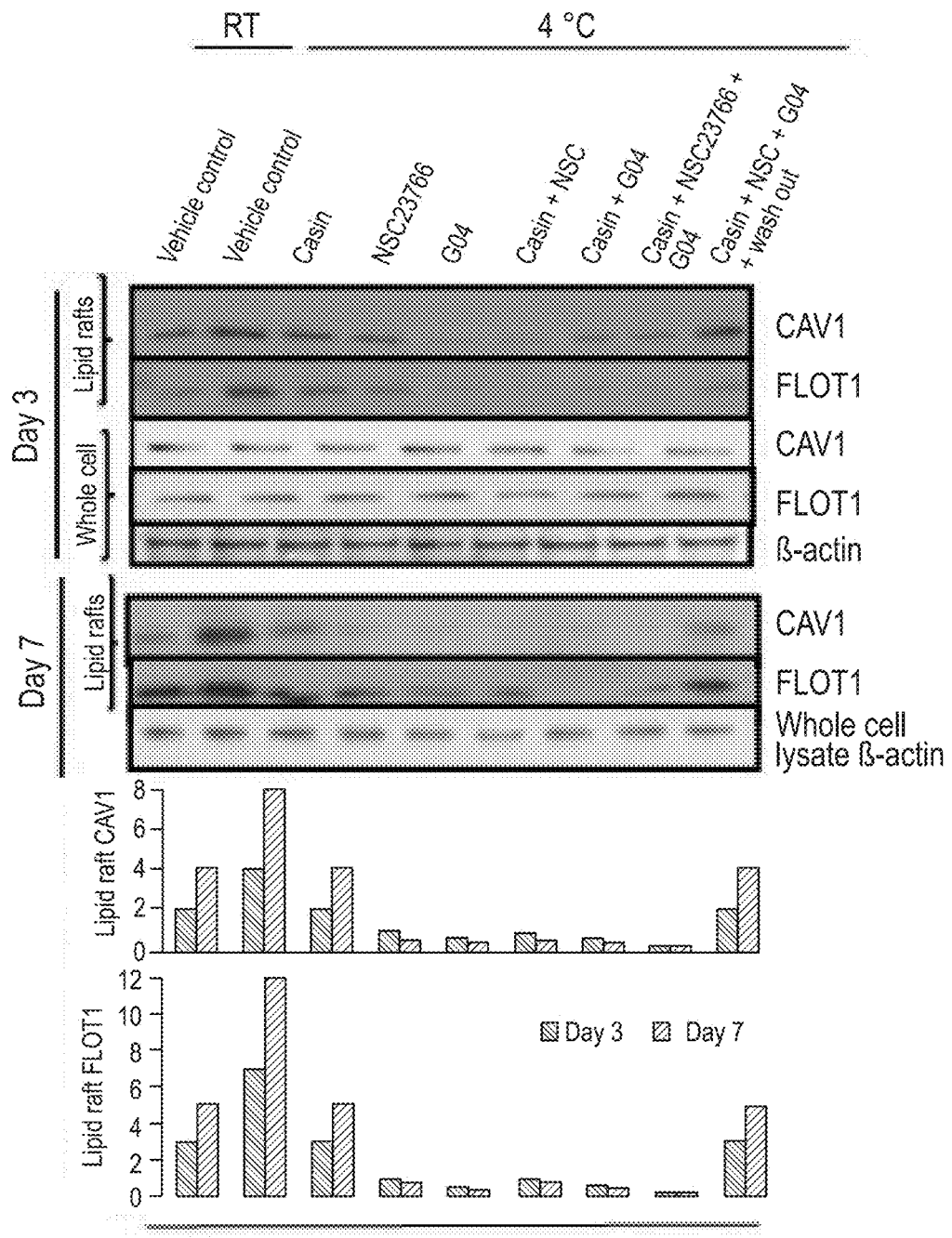
FIG. 9 depicts amelioration of lipid raft formation by Rho GTPase inhibitor combinations. Platelets were stored at RT or 4° C. for 3 or 7 days in different combinations of inhibitors (50 μM NSC23766, 10 μM CASIN and/or 75 μM G04) or no drug (vehicle control) at RT or 4° C. Platelet lysates were analyzed in the presence (lipid rafts) or absence (whole cell lysate) of Triton-X-100 mediated extraction. Results are representative of two independent experiments with similar results. Lowe panels represent normalized quantification of lipid raft formation.

Finally, Rho family GTPase inhibitors can prevent human platelet storage lesion in vitro as assessed by microparticle formation and content of Gplb (CD42b) in microparticles. Applicant found that the use of inhibitors resulted in reversal of the refrigeration dependent microparticle generation (FIG. 8A-B). Finally, Applicant analyzed the formation of lipid raft microdomains on the platelet membrane by differential analysis in lysates enriched in Triton-X-100 resistant membrane fragments in human platelets stored refrigerated for 3 and 7 days (FIG. 9). We found a complete correlation between the results of survival of refrigerated platelets in presence of inhibitor combinations with the formation of lipid raft microdomains, suggesting that the inhibitor combination containing G04, NSC23766 and CASIN results in reversal of refrigeration-induced lipid raft formation. Interestingly, washing out G04, NSC23766 and CASIN results in restoration of the same levels of lipid rafts as found in 3 or 7 day stored platelets at room temperature (FIG. 9), suggesting that the removal of these inhibitors results in platelet membrane rheological modifications similar to the ones observed in unprocessed, standard storage platelets for the same period of time (FIG. 9). These data provide proof-of-concept that the long-term storage (6 days) of platelets in plasma containing Rho GTPase inhibitors is not deleterious of platelets but can further prevent their storage lesion-associated activation.

Thus, Applicant's data strongly support that reversible inhibition of multiple Rho family of GTPases by chemical inhibitors can significantly prevent refrigerated storage damage and improve platelet survival and transfusion function after refrigeration by interference with lipid raft microdomain formation, actomyosin dynamics and GPIb clustering in membrane microdomains.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for improving platelet survival upon transfusion comprising:
   contacting platelets with a RHOA inhibitor selected from:

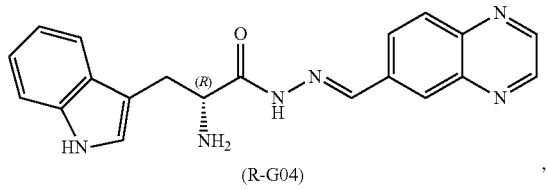

or pharmaceutically acceptable salt thereof,

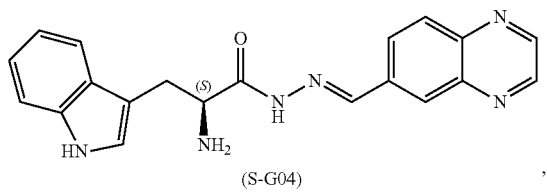

or pharmaceutically acceptable salt thereof, or combinations thereof; and
infusing said contacted platelets into a subject.

2. The method of claim 1, wherein said RHOA inhibitor is present at a concentration of from about 1 µM to about 500 µM.

3. The method of claim 1, wherein the platelets are stored in the presence of the RHOA inhibitor at a temperature of from about 1° C. to about 25° C.

4. The method of claim 1, wherein the platelets are stored in the presence of the RHOA inhibitor for a period of time of from about 3 to 20 days.

5. The method of claim 1, wherein the platelets are further contacted with a physiologically acceptable carrier.

6. The method of claim 5, wherein said physiologically acceptable carrier is selected from saline, phosphate buffered saline, Tris buffered saline, Hank's buffered saline, water, or a combination thereof.

7. The method according to claim 5, wherein said physiologically acceptable carrier comprises an electrolyte solution.

8. A method for improving platelet survival upon transfusion comprising infusing treated platelets into a subject, wherein, prior to said infusing, the platelets have been treated by contacting platelets with a RHOA inhibitor selected from:

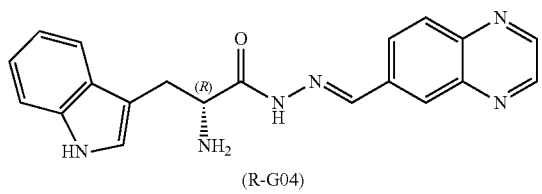

or pharmaceutically acceptable salt thereof,

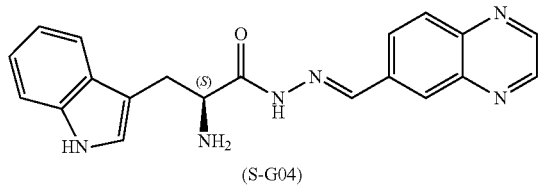

or pharmaceutically acceptable salt thereof, or combinations thereof.

9. The method of claim 8, wherein said RHOA inhibitor is present at a concentration of from about 1 µM to about 500 µM.

10. The method of claim 8, wherein the platelets are stored in the presence of the RHOA inhibitor at a temperature of from about 1° C. to about 25° C.

11. The method of claim 8, wherein the platelets are stored in the presence of the RHOA inhibitor for a period of time of from about 3 to 20 days.

12. The method of claim 8, wherein, prior to said infusing, the platelets have further been contacted with a physiologically acceptable carrier.

13. The method of claim 12, wherein said physiologically acceptable carrier is selected from saline, phosphate buffered saline, Tris buffered saline, Hank's buffered saline, water, or a combination thereof.

14. The method according to claim 12, wherein said physiologically acceptable carrier comprises an electrolyte solution.

15. A method for slowing platelet damage comprising: contacting platelets with a RHOA inhibitor selected from:

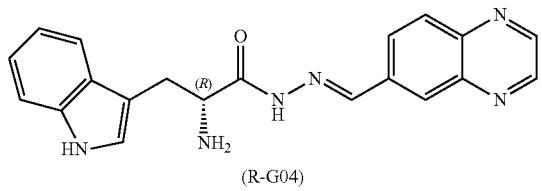

(R-G04), or pharmaceutically acceptable salt thereof,

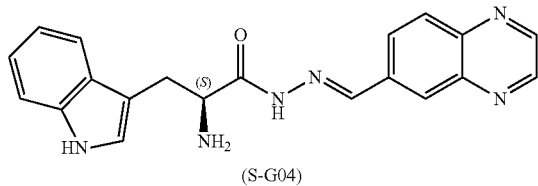

(S-G04), or pharmaceutically acceptable salt thereof, or combinations thereof.

16. The method of claim 15, wherein said RHOA inhibitor is present at a concentration of from about 1 µM to about 500 µM.

17. The method of claim 15, wherein the platelets are stored in the presence of the RHOA inhibitor at a temperature of from about 1° C. to about 25° C.

18. The method of claim 15, wherein the platelets are stored in the presence of the RHOA inhibitor for a period of time of from about 3 to 20 days.

19. The method of claim 15, wherein the platelets are further contacted with a physiologically acceptable carrier.

20. The method of claim 19, wherein said physiologically acceptable carrier is selected from saline, phosphate buffered saline, Tris buffered saline, Hank's buffered saline, water, or a combination thereof.

21. The method according to claim 19, wherein said physiologically acceptable carrier comprises an electrolyte solution.

22. The method of claim 15, wherein platelet damage is slowed such that platelet survival is greater than about 65% after a storage period of 24 hours at 5° C.

23. The method of claim 15, wherein platelet damage is slowed such that platelet survival is greater than about 95% after a storage period of 24 hours at 5° C.

24. A composition for cold platelet storage at 1° C. to 25° C. comprising platelets; a RHOA inhibitor selected from:

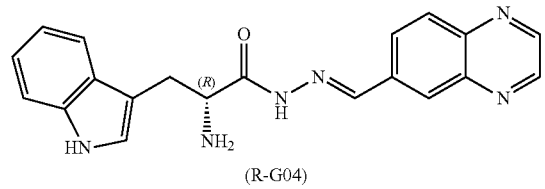

(R-G04), or pharmaceutically acceptable salt thereof,

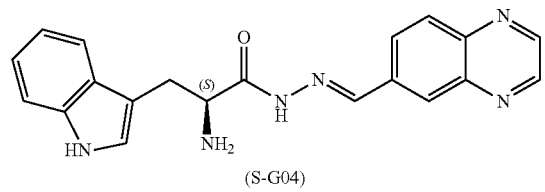

(S-G04), or pharmaceutically acceptable salt thereof, or combinations thereof; and
an additional therapeutic agent.

25. The composition of claim 24, further comprising a physiologically acceptable carrier.

26. The composition of claim 25, wherein the carrier is selected from saline, phosphate buffered saline, Tris buffered saline, Hank's buffered saline, water, or a combination thereof.

27. The composition according to claim 25, wherein said carrier comprises an electrolyte solution.

28. The composition of claim 24, further comprising sodium ion, potassium ion, acetate ion, magnesium ion, chloride ion, gluconate ion, glucose, phosphate ion, citrate ion and calcium ion.

29. The composition of claim 24, further comprising Hepes buffered saline or Tris buffered saline.

* * * * *